US012590061B2

(12) United States Patent
Liu et al.

(10) Patent No.: US 12,590,061 B2
(45) Date of Patent: Mar. 31, 2026

(54) CRYSTALLINE FORM OF ACETYLCHOLINESTERASE INHIBITOR AND PREPARATION METHOD THEREFOR AND APPLICATION THEREOF

(71) Applicants: SHANGHAI INSTITUTE OF MATERIA MEDICA, CHINESE ACADEMY OF SCIENCES, Shanghai (CN); JIANGSU KANION PHARMACEUTICAL CO., LTD., Lianyungang (CN)

(72) Inventors: Hong Liu, Shanghai (CN); Yu Zhou, Shanghai (CN); Haiyan Zhang, Shanghai (CN); Yan Fu, Shanghai (CN); Jian Li, Shanghai (CN); Hualiang Jiang, Shanghai (CN); Xican Tang, Shanghai (CN); Kaixian Chen, Shanghai (CN)

(73) Assignees: SHANGHAI INSTITUTE OF MATERIA MEDICA, CHINESE ACADEMY OF SCIENCES, Shanghai (CN); JIANGSU KANION PHARMACEUTICAL CO., LTD., Lianyungang (CN)

( * ) Notice: Subject to any disclaimer, the term of this patent is extended or adjusted under 35 U.S.C. 154(b) by 905 days.

(21) Appl. No.: 17/780,449

(22) PCT Filed: Nov. 24, 2020

(86) PCT No.: PCT/CN2020/131119

§ 371 (c)(1),
(2) Date: May 26, 2022

(87) PCT Pub. No.: WO2021/104257

PCT Pub. Date: Jun. 3, 2021

(65) Prior Publication Data

US 2023/0010368 A1 Jan. 12, 2023

(30) Foreign Application Priority Data

Nov. 26, 2019 (CN) ......................... 201911176960.2

(51) Int. Cl.
*C07D 211/38* (2006.01)

(52) U.S. Cl.
CPC ........ *C07D 211/38* (2013.01); *C07B 2200/13* (2013.01)

(58) Field of Classification Search
CPC ........ A61P 25/00; A61P 25/28; C07D 211/38; C07B 2200/13
See application file for complete search history.

(56) References Cited

U.S. PATENT DOCUMENTS

| | | | | |
|---|---|---|---|---|
| 9,637,454 | B2 * | 5/2017 | Liu | A61P 25/28 |
| 2015/0225343 | A1 | 8/2015 | Cheng | |

FOREIGN PATENT DOCUMENTS

| | | | | |
|---|---|---|---|---|
| CN | 103787954 B | 1/2016 | | |
| CN | 107200706 A | 9/2017 | | |
| WO | 1999029668 A1 | 6/1999 | | |
| WO | 2010071216 A1 | 6/2010 | | |
| WO | 2014008629 A1 | 1/2014 | | |
| WO | WO-2014063587 A1 * | 5/2014 | | A61K 31/445 |

OTHER PUBLICATIONS

Machine Translation of WO2014063587 (Year: 2014).*
Chen, Jiangliang et al., "Several Crystallization Methods and Their Application Progress," Guangzhou Chemical Industry, vol. 47, No. 17, Sep. 30, 2019, pp. 49-51, 4 pages.
Maryam Farrokhnia et al., "Marine Natural Products as Acetylcholinesterase Inhibitor: Comparative Quantum Mechanics and Molecular Docking Study," Current Computer-Aided Drug Design, vol. 10, No. 1, May 1, 2014, pp. 83-95, 13 pages.
The International Search Report of PCT Application No. PCT/CN2020/131119 mailed Jan. 27, 2021 with English Translation.
Ashizawa, Kazuhide, "Physico-Chemical Studies on the Molecular Details of Drug Crystals", Pharm Tech Japan, vol. 18, 2002, pp. 1-16.
Terada, Katsuhide, "Application of Thermal Analysis to the Pharmaceutical Development", Heat Measurement, vol. 38, No. 2, 2022, pp. 46-53.

* cited by examiner

*Primary Examiner* — Jeffrey H Murray
*Assistant Examiner* — Daniel John Burkett
(74) *Attorney, Agent, or Firm* — NKL Law; Bin Lu; Allen Xue

(57) ABSTRACT

The present invention provides a crystalline form of an acetylcholinesterase inhibitor, a preparation method therefor and application thereof. Specifically, the crystalline form is crystalline form A, crystalline form B and crystalline form C of 2-((1-(2-fluorobenzyl)-4-fluoropiperidin-4-yl) methylene)-5, 6-dimethoxy-2, 3-dihydro-1-indanone. The crystalline form of the present invention does not contain water and solvent, has high stability and low hygroscopicity, is easy to process, and is very suitable for preparing drugs for preventing and/or treating neurodegenerative diseases.

10 Claims, 15 Drawing Sheets

CRYSTALLINE FORM OF ACETYLCHOLINESTERASE INHIBITOR AND PREPARATION METHOD THEREFOR AND APPLICATION THEREOF

RELATED APPLICATIONS

This application is a U.S. National Stage Application under 35 U.S.C. 371 of International Patent Application No.: PCT/CN2020/131119, filed Nov. 24, 2020, which claims priority to Chinese Patent Application No.: 201911176960.2, filed Nov. 26, 2019.

TECHNICAL FIELD

The invention relates to the field of pharmaceutical chemistry, in particular to a crystalline form of acetylcholinesterase inhibitor 2-(1-(2-fluorobenzyl)-4-fluoropiperidin-4-yl) methylene)-5, 6-dimethoxy-2, 3-dihydro-1-indanone, and preparation method therefor and application thereof.

BACKGROUND 2-((1-(2-fluorobenzyl)-4-fluoropiperidin-4-yl)methylene)-5,6-dimethoxy-2, 3-dihydro-1-indanone (compound of formula I) is a new acetylcholinesterase (AChE) inhibitor with a new mechanism of "fast binding and slow dissociation", the preparation method and pharmacological activity thereof are disclosed in WO2014/063587.

I

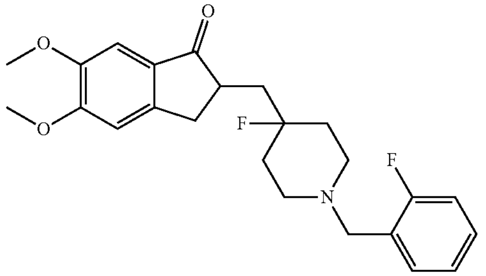

Acetylcholinesterase catalyzes the cleavage reaction of acetylcholine, results in the loss of acetylcholine and the failure of nerve signal transduction, and then leads to the decline of cognitive function and the loss of memory ability, which are clinically manifested as symptoms of Alzheimer's disease. Acetylcholinesterase inhibitors can inhibit AChE activity, delay the hydrolysis rate of acetylcholine, increase the level of acetylcholine in the synaptic cleft, and ensure the normal conduction of nerve signal, thereby playing a therapeutic role in Alzheimer's disease and other related diseases.

Since different crystalline forms of a drug may affect in vivo dissolution and absorption thereof, and then may affect the clinical efficacy and safety of the drug to a certain extent, especially for some insoluble oral solid or semi-solid preparations, the influence of the crystalline form will become greater.

Therefore, it is necessary to develop the crystalline form of the compound of formula I with high stability and low hygroscopicity and being convenient for processing.

SUMMARY OF THE INVENTION

The purpose of the present invention is to provide a crystalline form of a compound of formula I with high stability and low hygroscopicity, and being convenient for processing.

In the first aspect of the present invention, provided is a crystalline form of the compound of formula I, wherein the crystalline form is selected from the group consisting of Form A, Form B and Form C,

I

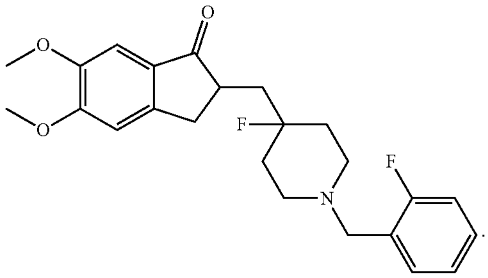

In another preferred embodiment, the X-ray powder diffraction pattern of Form A has characteristic peaks at three or more 2θ values selected from the group consisting of 14.914±0.2°, 15.593±0.2°, 17.617±0.2°, 18.022±0.2°, 19.525±0.2°, 20.806±0.2°.

In another preferred embodiment, the X-ray powder diffraction pattern of the Form A further has characteristic peaks at one or more 2θ values selected from the group consisting of 6.006±0.2°, 6.809±0.2°, 17.12±0.2°, 20.028±0.2°, 20.506±0.2°, 21.463±0.2°, 21.99±0.2° and 25.918±0.2°.

In another preferred embodiment, the X-ray powder diffraction pattern of the Form A further has characteristic peaks at one or more 2θ values selected from the group consisting of 8.777±0.2°, 14.672±0.2°, 15.95±0.2°, 16.539±0.2°, 18.578±0.2° and 19.123±0.2°.

In another preferred embodiment, the X-ray powder diffraction pattern of the Form A has characteristic peaks at 2θ values substantially as shown in Table 1, wherein the 2θ values of each peak has an error margin of ±0.2°.

In another preferred embodiment, the Form A has an XRPD pattern substantially as shown in FIG. 2.

In another preferred embodiment, the Form A has one or more features selected from the group consisting of:

1) the TG pattern of the Form A shows no weight loss before the decomposition of the compound of formula I;
2) the DSC pattern of the Form A has a characteristic absorption peak at a peak of 123±5° C. (or ±3° C., or 1° C.);
3) the Form A has a moisture-absorption weight gain of ≤1%, preferably 0.6%±0.2%, under a relative humidity of 0-95%.

In another preferred embodiment, the IR pattern of Form A includes three or more of the following characteristic absorption peaks represented by wavelength λ: 2952±2 $cm^{-1}$, 2922±2 $cm^{-1}$, 2817±2 $cm^{-1}$, 1693±2 $cm^{-1}$, 1604±2 $cm^{-1}$, 1589±2 $cm^{-1}$, 1498±2 $cm^{-1}$, 1454±2 $cm^{-1}$, 1365±2 $cm^{-1}$, 1315±2 $cm^{-1}$, 1265±2 $cm^{-1}$, 1223±2 $cm^{-1}$, 1118±2 $cm^{-1}$, 1039±2 $cm^{-1}$, 762±2 $cm^{-1}$, preferably, each of the characteristic absorption peaks have an error margin of ±1 $cm^{-1}$.

In another preferred embodiment, the Raman spectrum pattern of Form A includes three or more of the following characteristic absorption peaks represented by Raman shifts: 748.48±2 $cm^{-1}$, 1314.84±2 $cm^{-1}$, 1364.11±2 $cm^{-1}$, 1443.39±2 $cm^{-1}$, 1456.10±2 $cm^{-1}$, 1590.10±2 $cm^{-1}$, 1684.81±2 $cm^{-1}$, 2922.05±2 $cm^{-1}$, 2953.62±2 $cm^{-1}$, preferably, each of the characteristic absorption peaks has an error margin of 1 $cm^{-1}$.

In another preferred embodiment, the Form A has one or more features selected from the group consisting of:

1) the Form A has a TG pattern substantially as shown in FIG. 3;
2) the Form A has a DSC pattern substantially as shown in FIG. 4;
3) the Form A has a DVS pattern substantially as shown in FIG. 5;
4) the Form A has an IR pattern substantially as shown in FIG. 6; and/or
5) the Form A has a Raman pattern substantially as shown in FIG. 7.

In another preferred embodiment, the X-ray powder diffraction pattern of the Form B has characteristic peaks at three or more 2θ values selected from the group consisting of 6.004±0.2°, 14.927±0.2°, 16.551±0.2°, 20.503±0.2° and 21.967±0.2°.

In another preferred embodiment, the X-ray powder diffraction pattern of the Form B further has characteristic peaks at one or more 2θ values selected from the group consisting of 11.7±0.2°, 15.898±0.2°, 17.816±0.2°, 18.54±0.2°, 19.843±0.2°, 22.653±0.2° and 24.575±0.2°.

In another preferred embodiment, the X-ray powder diffraction pattern of the Form B further has characteristic peaks at one or more 2θ values selected from the group consisting of 12.94±0.2°, 15.371±0.2°, 18.0±0.2°, 21.47±0.2° and 25.562±0.2°.

In another preferred embodiment, the X-ray powder diffraction pattern of the Form B has characteristic peaks at 2θ values substantially as shown in Table 2, wherein the 2θ value of each peaks has an error margin of ±0.2°.

In another preferred embodiment, the Form B has one or more features selected from the group consisting of:

1) the TG pattern of the Form B shows no weight loss before the decomposition of the compound of formula I;
2) the DSC pattern of the Form B has a characteristic absorption peak at a peak of 122.5±5° C. (or ±3° C., or 1° C.);
3) the Form B has a moisture-absorption weight gain of ≤1.5%, preferably, 1%±0.2%, more preferably, 1%±0.1%, under a relative humidity of 0-95%.

In another preferred embodiment, the Form B has one or more features selected from the group consisting of:

1) the Form B has a TG pattern substantially as shown in FIG. 10;
2) the Form B has a DSC pattern substantially as shown in FIG. 11;
3) the Form B has a DVS pattern substantially as shown in FIG. 12;
4) the Form B has an IR pattern substantially as shown in FIG. 13;
5) the Form B has a Raman pattern substantially as shown in FIG. 14;
6) the Form B has an XRPD pattern substantially as shown in FIG. 9.

In another preferred embodiment, the X-ray powder diffraction pattern of the Form C has characteristic peaks at three or more 2θ values of selected from the group consisting of 15.473±0.2°, 15.832±0.2°, 18.459±0.2°, 18.824±0.2°, 20.864±0.2°, 22.331±0.2°, and 24.374±0.2°.

In another preferred embodiment, the X-ray powder diffraction pattern of the Form C further has characteristic peaks at one or more 2θ values selected from the group consisting of 6.527±0.2°, 14.891±0.2°, 16.833±0.2°, 19.164±0.2°, 19.625±0.2°, 22.709±0.2°, 23.231±0.2°, and 27.703±0.2°.

In another preferred embodiment, the Form C has an X-ray powder diffraction pattern with characteristic peaks at 2θ values substantially as shown in Table 3, wherein the 2θ value of each peak has an error margin of ±0.2°.

In another preferred embodiment, the Form C has one or more features selected from the group consisting of:

1) the decomposition temperature of the Form C is 210±5° C. (or ±3° C., or ±1° C.);
2) the DSC pattern of the Form C has a characteristic absorption peak at a peak of 124±5° C. (or −3° C., or −1° C.);
3) the Form C has a moisture-absorption weight gain of ≤1.5%, preferably 1.2%±0.2%, under a relative humidity of 0-95%.

In another preferred embodiment, the Form C has one or more features selected from the group consisting of:

1) the Form C has a TG pattern substantially as shown in FIG. 17;
2) the Form C has a DSC pattern substantially as shown in FIG. 18;
3) the Form C has a DVS pattern substantially as shown in FIG. 19;
4) the Form C has an IR pattern substantially as shown in FIG. 20;
5) the Form C has a Raman pattern substantially as shown in FIG. 21; and/or
6) the Form C has an XRPD pattern substantially as shown in FIG. 16.

In the second aspect of the present invention, provided is a crystalline composition comprising the Form A, the Form B, the Form C, or a combination thereof according to the first aspect of the present invention.

In another preferred embodiment, the weight percentage of Form A is 60-99.999%, preferably 80-99.999%, more preferably 90-99.999%, based on the total weight of the crystalline composition.

In another preferred embodiment, the crystalline composition further comprises: a crystalline form of the compound of formula I other than Form A-C, or an amorphous form of compound of formula I.

In the third aspect of the present invention, provided is a method for preparing the crystalline form according to the first aspect of the present invention, including the step of providing a solution of the compound of formula I in an inert solvent, volatilizing the solvent, and obtaining the crystalline form.

In another preferred embodiment, the volatilization temperature is 10-60° C., preferably 20-50° C.

In another preferred embodiment, the volatilization time is from 1 h to 5 days, preferably from 1 to 3 days.

In another preferred embodiment, the crystalline form is Form A, and the inert solvent is selected from the group consisting of water, alcohols, ethers, ketones, acetonitrile, THF, ethyl acetate, nitromethane, and combinations thereof, provided that the inert solvent is not a mixed solvent of ethyl acetate, water, and methanol.

In another preferred embodiment, the crystalline form is Form B, and the inert solvent is selected from the group consisting of toluene, a mixed solvent of methanol and methyl isobutyl ketone, a mixed solvent of acetone and methyl isobutyl ketone, a mixed solvent of THF and toluene, a mixed solvent of toluene and ethanol, and a mixed solvent of toluene, water and methanol.

In another preferred embodiment, the crystalline form is Form C, and the inert solvent is selected from the group consisting of ethyl acetate, a mixed solvent of water and methanol, and a mixed solvent of methanol and toluene.

In another preferred embodiment, provided is a method for preparing Form A, comprising the steps of: suspending the compound of formula I in a first inert solvent, stirring, and filtering, thereby obtaining the Form A.

In another preferred embodiment, the first inert solvent is selected from the group consisting of alcohols, ethers, alkanes, and combinations thereof.

In another preferred embodiment, the weight-volume ratio of the compound of formula I in the first inert solvent is 10-100 mg/mL, preferably 15-50 mg/mL, more preferably 20-40 mg/mL.

In another preferred embodiment, the alcohols is a C1-C10 alcohol, preferably a C1-C8 alcohol, more preferably a C1-C5 alcohol; more preferably, methanol, ethanol, n-propanol, isopropanol, n-butanol, isoamyl alcohol, or combinations thereof.

In another preferred embodiment, the ethers are C2-C10 ethers, preferably methyl tert-butyl ether, diethyl ether, or combinations thereof.

In another preferred embodiment, the alkanes is a C5-C12 alkane, preferably n-pentane, n-hexane, or a combination thereof.

In another preferred embodiment, the stirring has one or more features selected from the group consisting of:

(1) the stirring time is 12-48 h, preferably 18-36 h;

(2) the stirring temperature is 25±5° C.

In the fourth aspect of the present invention, provided is a method for preparing the Form A according to the first aspect of the present invention, including the steps of:

heating to dissolve the compound of formula I in a second inert solvent, crystallizing by cooling, thereby obtaining the Form A.

In another preferred embodiment, the temperature for heating to dissolve is 50-70° C., preferably 55-65° C.

In another preferred embodiment, the temperature for crystallizing by cooling is −10-10° C., preferably −4-0° C.

In another preferred embodiment, the second inert solvent is selected from the group consisting of alcohols, ethers, and combinations thereof.

In another preferred embodiment, the weight-volume ratio of the compound of formula I in the second inert solvent is from 1 to 100 mg/mL, preferably from 1 to 50 mg/mL, more preferably from 5 to 40 mg/mL.

In another preferred embodiment, the alcohols are C1-C10 alcohol, preferably a C1-C8 alcohol, more preferably a C1-C5 alcohol; preferably, methanol, ethanol, n-propanol, isopropanol, n-butanol, isoamyl alcohol, or combinations thereof.

In another preferred embodiment, the ethers are C2-C10 ethers, preferably methyl tert-butyl ether, diethyl ether, or combinations thereof.

In the fifth aspect of the present invention, provided is a method for preparing the Form A according to the first aspect of the present invention, including the steps of:

dissolving the compound of formula I in a third inert solvent, and then adding a poor solvent, crystallizing, thereby obtaining the Form A.

In another preferred embodiment, the third inert solvent (good solvent) is selected from the group consisting of ketones, esters, tetrahydrofuran, toluene, and combinations thereof.

In another preferred embodiment, the ketones are selected from the group consisting of methyl ethyl ketone, acetone, methyl isobutyl ketone, and combinations thereof.

In another preferred embodiment, the esters are selected from the group consisting of ethyl acetate, ethyl propionate, ethyl butyrate, ethyl valerate, ethyl caproate, and combinations thereof.

In another preferred embodiment, the poor solvent is selected from the group consisting of alkanes, ethers, and combinations thereof.

In another preferred embodiment, the alkanes are C5-C12 alkane, preferably n-pentane, n-hexane, petroleum ether, and combinations thereof.

In another preferred embodiment, the ethers are C2-C10 ethers, preferably methyl tert-butyl ether, diethyl ether, or combinations thereof.

In the sixth aspect of the present invention, provided is a pharmaceutical composition comprising the crystalline form according to the first aspect of the present invention, and a pharmaceutically acceptable carrier.

In another preferred embodiment, the pharmaceutical composition comprises Form A, Form B, Form C, or combinations thereof.

In another preferred embodiment, the carrier is selected from the group consisting of a filler, a disintegrant, a lubricant, and combinations thereof.

In another preferred embodiment, the filler is selected from the group consisting of pregelatinized starch, lactose, microcrystalline cellulose, dextrin, mannitol, magnesium oxide, calcium sulfate, and combinations thereof.

In another preferred embodiment, the disintegrant is selected from the group consisting of carboxymethyl cellulose and salts thereof, cross-linked carboxymethyl cellulose and salts thereof, cross-linked povidone, sodium carboxymethyl starch, low-substituted hydroxypropyl cellulose, and combinations thereof.

In another preferred embodiment, the lubricant is selected from the group consisting of magnesium stearate, calcium stearate, and combinations thereof.

In the seventh aspect of the present invention, provided is a use of a crystalline form according to the first aspect of the present invention or the crystalline composition according to the second aspect of the present invention or a pharmaceutical composition according to the fifth aspect of the present invention for manufacturing a medicament for prevention and/or treatment of neurological diseases associated with acetylcholinesterase.

In another preferred embodiment, the neurological disease associated with acetylcholinesterase is neurodegenerative disease, Parkinson's syndrome, epilepsy or schizophrenia.

In another preferred embodiment, provided is a use of a crystalline form according to the first aspect of the invention or a crystalline composition according to the second aspect of the invention or a pharmaceutical composition according to the fifth aspect of the invention for manufacturing a medicament for prevention and/or treatment of neurodegenerative diseases.

In another preferred embodiment, the neurodegenerative disease is selected from the group consisting of senile dementia (such as Alzheimer's disease), cerebrovascular dementia, attention deficit hyperactivity disorder, and combinations thereof.

In the eighth aspect of the present invention, provided is a method for treating a neurodegenerative disease, comprising a step of administering to a patient therapeutically effective amount of the crystalline form according to the first aspect of the present invention or the product according to the second aspect of the present invention or the pharmaceutical composition according to the sixth aspect of the present invention.

It should be understood that within the scope of the present invention, the above-mentioned technical features of the present invention and the technical features specifically described in the following (such as embodiments) can be combined with each other to form a new or preferred technical solution. Limited to space, it is not repeated here.

DETAILED DESCRIPTION OF THE INVENTION

Figure 1:
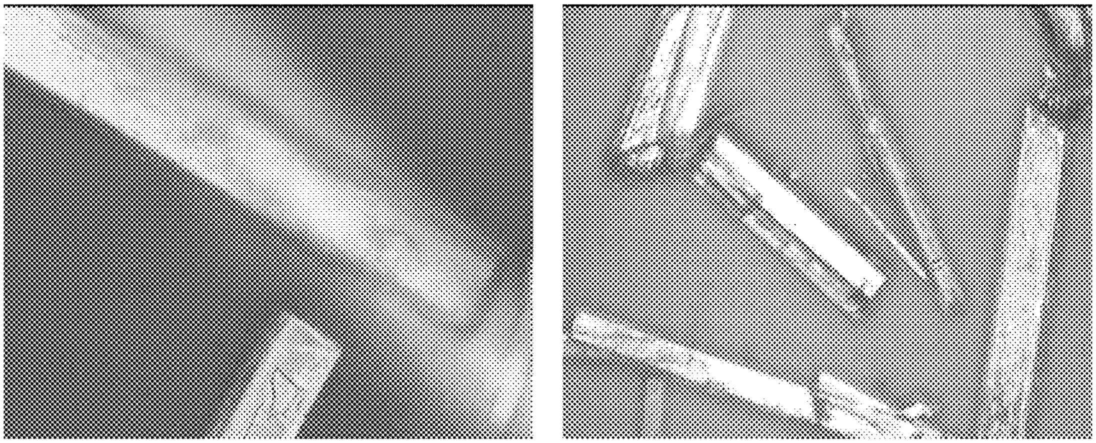
FIG. 1 is a polarizing microscope photograph of Form A of Example 1 (10*10 left and 10*5 right).

After extensively and intensively studying, and extensive screening and testing, the present inventors provide crystalline forms A-C of the compound of Formula I, which contain no water and solvents, have high stability and low hygroscopicity, are easy to process, and are suitable for medicines. On this basis, the present invention was completed.

Terms

Unless otherwise defined, all technical and scientific terms used herein have the same meaning as normally be understood by those of ordinary skill in the art to which the present invention belongs.

As used herein, when used in reference to a specifically enumerated value, the term "about" is intended to mean that the value can vary from the enumerated value by no more than 1%. For example, as used herein, the expression "about 100" includes all values between 99 and 101 (e.g., 99.1, 99.2, 99.3, 99.4, etc.).

As used herein, the terms "contain" or "include (comprise)" may be open-ended, semi-closed, and closed-ended. In other words, the term also includes "essentially consist of", or "consist of".

As described herein, the terms "compound of formula I", and "2-((1-(2-fluorobenzyl)-4-fluoropiperidin-4-yl)methylene)-5,6-dimethoxy-2, 3-dihydro-1-indanone" are used interchangeably to refer to compounds having the structure of formula I.

As used herein, the term "n or more" refers to including n and any positive integer greater than n (e. g., n, n+1, . . . ), where the upper limit Nup is the number of all values in the group. For example, "1 or more" does not only include each positive integer of 1, 2, 3, 4, 5, 6, 7, 8, 9, 10, 11, 12, 13, 14, 15, 16, 17, 18, 19, 20, 21, . . . and upper limit Nup, but also includes ranges such as "2 or more", "3 or more", "4 or more", "5 or more", "6 or more", "7 or more", "8 or more", "9 or more", "10 or more", "11 or more", "12 or more", "13 or more", "14 or more", "15 or more", etc. For example, "3 or more" not only includes each positive integer of 3, 4, 5, 6, 7, 8, 9, 10, 11, 12, 13, 14, 15, 16, 17, 18, 19, 20, 21, . . . and upper limit Nup, but also includes ranges such as "4 or more", "5 or more", "6 or more", "7 or more", "8 or more", "9 or more", "10 or more", "11 or more", "12 or more", "13 or more", "14 or more", "15 or more", etc.

As used herein, the term "inert solvent" refers to a solvent that does not react with the compound of formula I of the present invention. Preferably, none of the solvents used in the method for preparing crystalline form of the present invention react with the compound of formula I.

Unless otherwise specified, the term "room temperature" or "normal temperature" refers to a temperature of 4-32° C., preferably 25±5° C.

Polymorph

Solid is either presented in amorphous form or in crystalline form. In the case of crystalline form, the molecule is located in the three-dimensional lattice position. When a compound crystallizes from a solution or slurry, it can be crystallized in different spatial lattice arrayment (such property is called "polymorphic phenomenon") to form crystals with different crystalline forms. Such various crystalline forms are called "polymorphs". Different polymorphs of a given substance may differ from each other in one or more physical properties, such as solubility and dissolution rate, true specific gravity, crystalline form, stacking mode, fluidity, and/or solid-state stability.

The polymorph of the present invention is Form A, Form B, or Form C of the compound of Formula I.

As used herein, "Form A", "Form A of the compound of formula I", "Form A of the present invention", "Form A of 2-((1-(2-fluorobenzyl)-4-fluoropiperidin-4-yl) methylene)-5, 6-dimethoxy-2, 3-dihydro-1-indanone" can be used interchangeably, and refers to the Form A of 2-(1-(2-fluorobenzyl)-4-fluoropiperidin-4-yl)methylene)-5,6-dimethoxy-2, 3-dihydro-1-indanone (compound of formula I).

Form A

The invention provides the Form A of the compound of formula I,

I

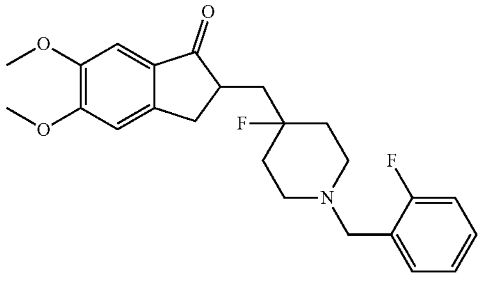

The X-ray powder diffraction pattern of the Form C has characteristic peaks at three or more 2θ values selected from the group consisting of 14.914±0.2°, 15.593±0.2°, 17.617±0.2°, 18.022±0.2°, 19.525±0.2°, and 20.806±0.2°.

In another preferred embodiment, the X-ray powder diffraction pattern of the Form A further has characteristic peaks at one or more 2θ values selected from the group consisting of 6.006±0.2°, 6.809±0.2°, 17.12±0.2°, 20.028±0.2°, 20.506±0.2°, 21.463±0.2°, 21.99±0.2°, and 25.918±0.2°.

In another preferred embodiment, the X-ray powder diffraction pattern of the Form A further has characteristic peaks at one or more 2θ values selected from the group consisting of 8.777±0.2°, 14.672±0.2°, 15.95±0.2°, 16.539±0.2°, 18.578±0.2° and 19.123±0.2°.

In another preferred embodiment, the X-ray powder diffraction pattern of the Form A has characteristic peaks at 2θ values substantially as shown in Table 1, wherein the 2θ values of each peak has an error margin of ±0.2°.

Figure 2:
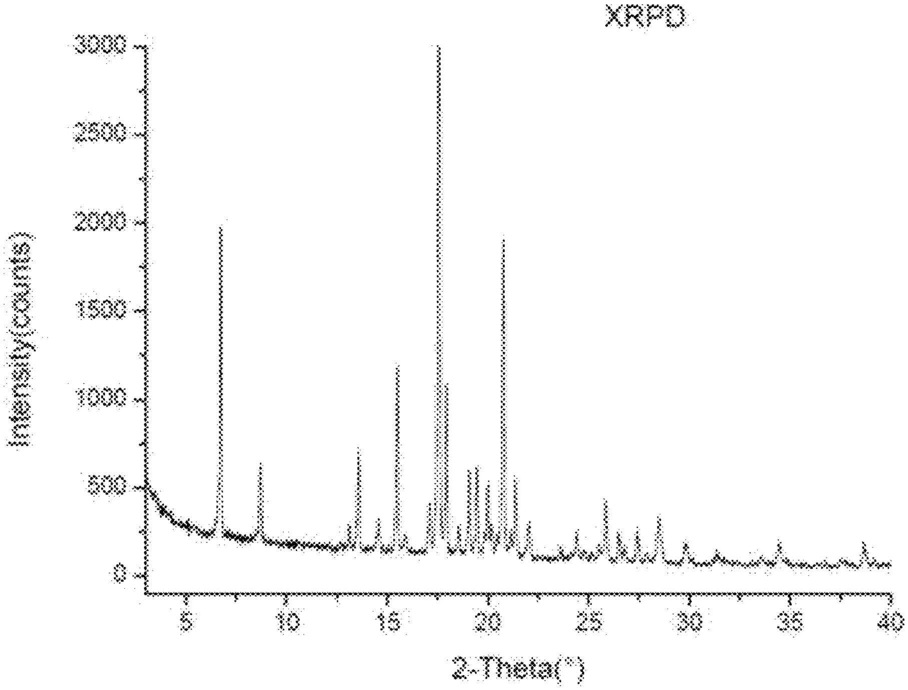
FIG. 2 is an XRD pattern of Form A of Example 1.

In another preferred embodiment, the Form A has an XRPD pattern substantially as shown in FIG. 2.

In another preferred embodiment, the Form A has one or more features selected from the group consisting of:

1) the TG pattern of the Form A shows no weight loss before the decomposition of the compound of formula I;
2) the DSC pattern of the Form A has a characteristic absorption peak at a peak of 123±5° C. (or ±3° C., or ±1° C.);
3) the Form A has a moisture-absorption weight gain of ≤1% under a relative humidity of 0-95%, preferably 0.6% 0.2%.

In another preferred embodiment, the IR pattern of Form A includes there or more of the following characteristic absorption peaks represented by wavelength λ: 2952±2 $cm^{-1}$, 2922±2 $cm^{-1}$, 2817±2 $cm^{-1}$, 1693±2 $cm^{-1}$, 1604±2 $cm^{-1}$, 1589±2 $cm^{-1}$, 1498±2 $cm^{-1}$, 1454±2 $cm^{-1}$, 1365±2 $cm^{-1}$, 1315±2 $cm^{-1}$, 1265±2 $cm^{-1}$, 1223±2 $cm^{-1}$, 1118±2 $cm^{-1}$, 1039±2 $cm^{-1}$, 762±2 $cm^{-1}$, preferably, each of the characteristic absorption peaks has an error margin of 1 $cm^{-1}$.

In another preferred embodiment, the Raman spectrum pattern of Form A includes three or more of the following characteristic absorption peaks represented by Raman shifts: 748.48±2 $cm^{-1}$, 1314.84±2 $cm^{-1}$, 1364.11±2 $cm^{-1}$, 1443.39±2 $cm^{-1}$, 1456.10±2 $cm^{-1}$, 1590.10±2 $cm^{-1}$, 1684.81±2 $cm^{-1}$, 2922.05±2 $cm^{-1}$, 2953.62±2 $cm^{-1}$, preferably, each of the characteristic absorption peaks has an error margin of ±1 $cm^{-1}$.

Figure 3:
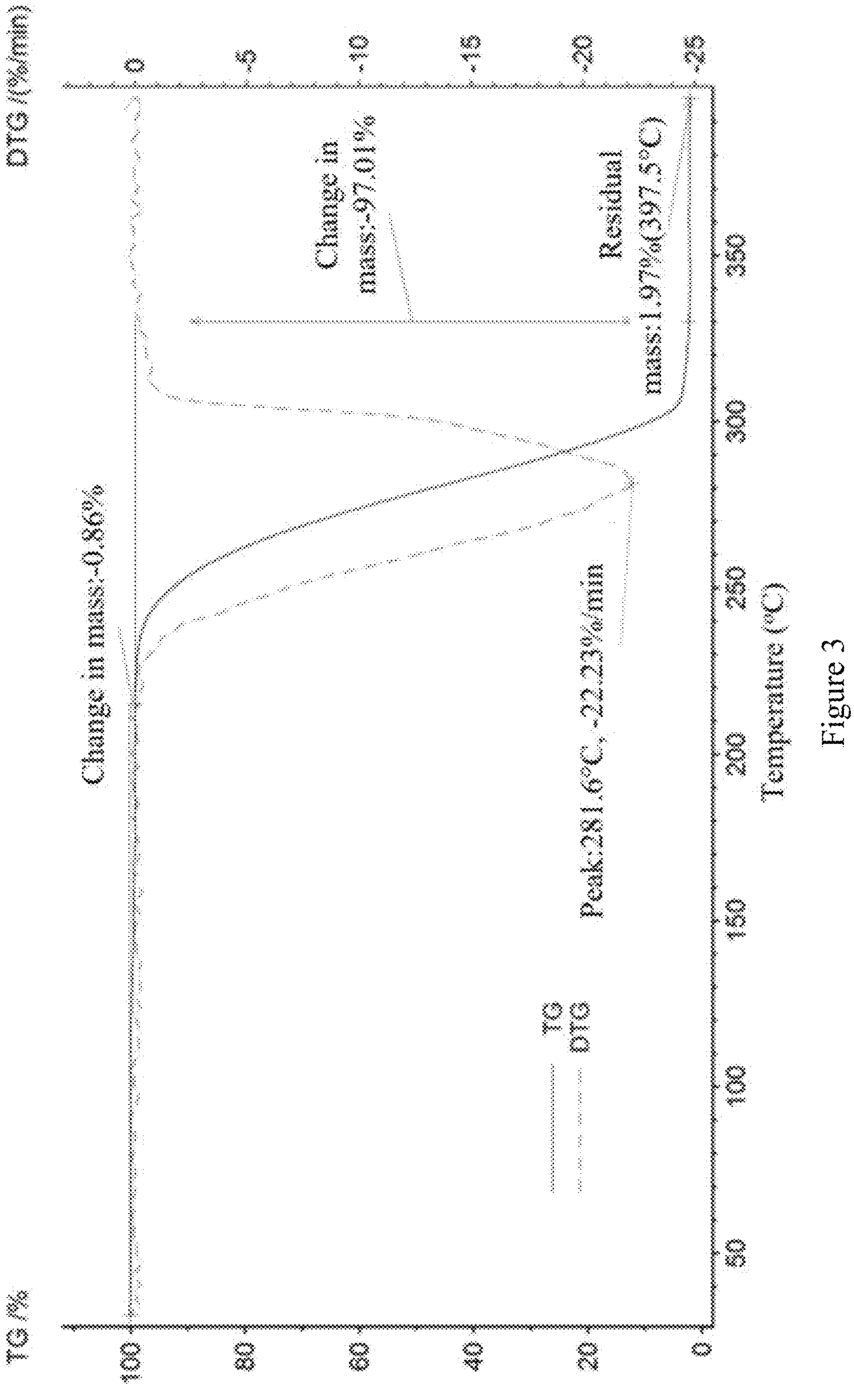
FIG. 3 is a TG pattern of the Form A of Example 1.
Figure 4:
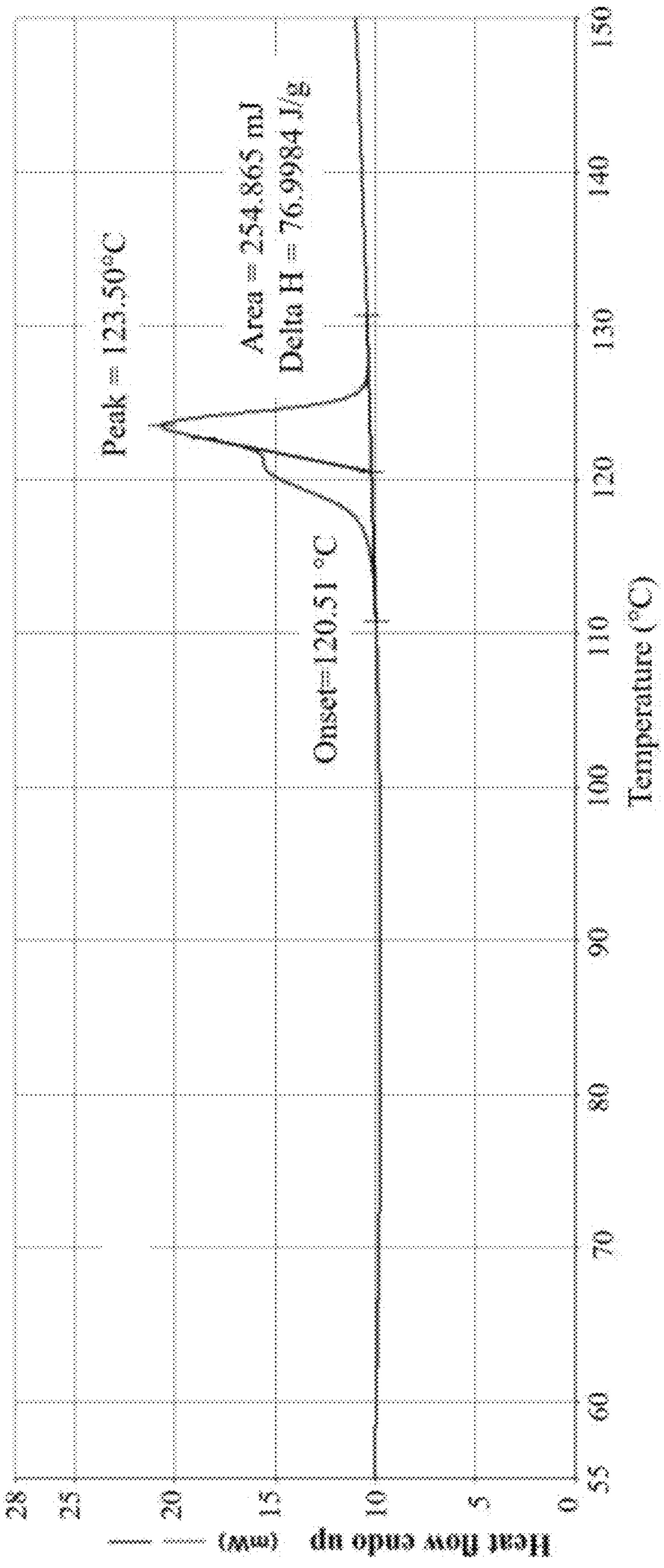
FIG. 4 is a differential scanning calorimetry (DSC) pattern of Form A of Example 1.
Figure 5:
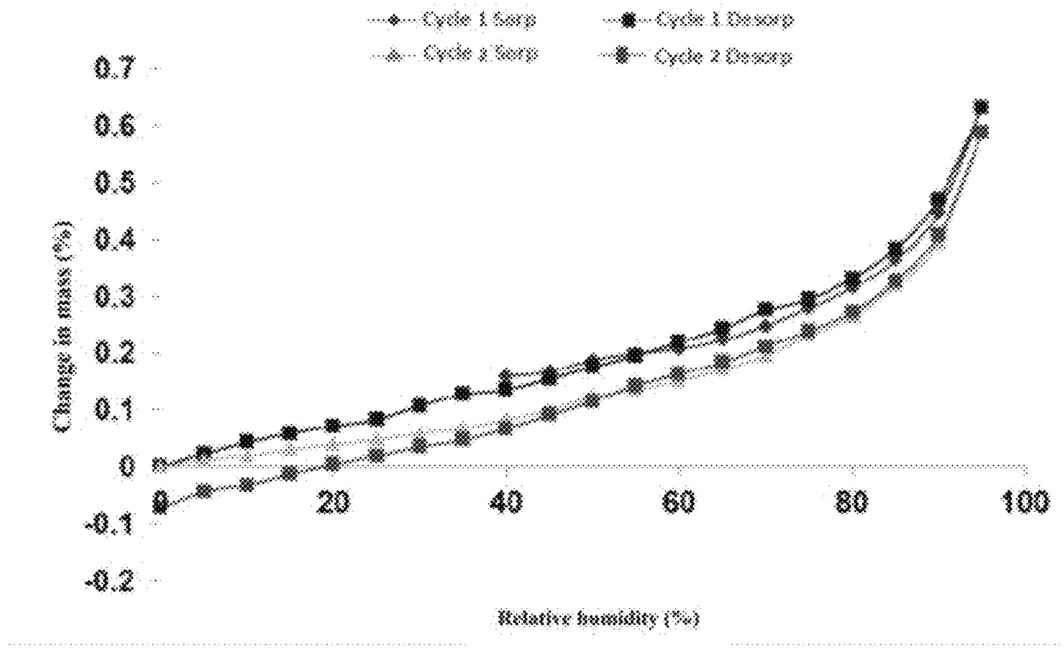
FIG. 5 is a dynamic vapor adsorption (DVS) pattern of Form A of Example 1.
Figure 6:
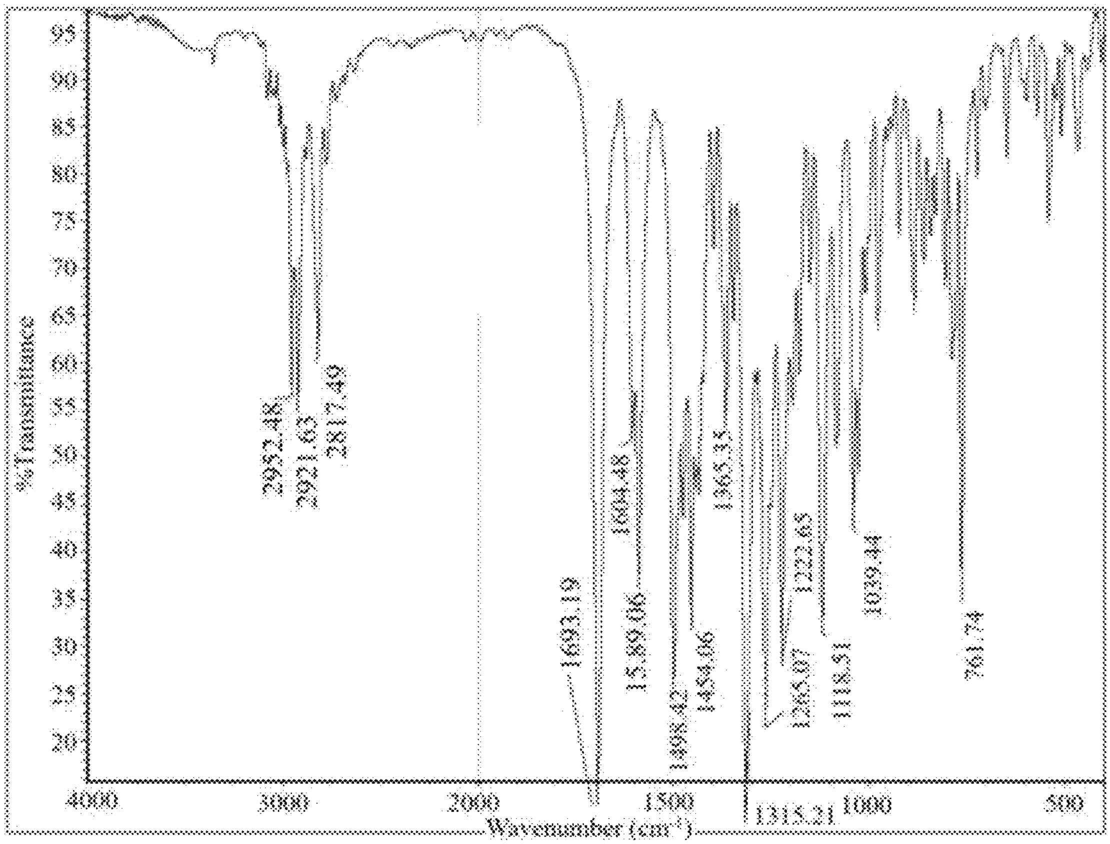
FIG. 6 is an infrared spectrum (IR) pattern of the Form A of Example 1.
Figure 7:
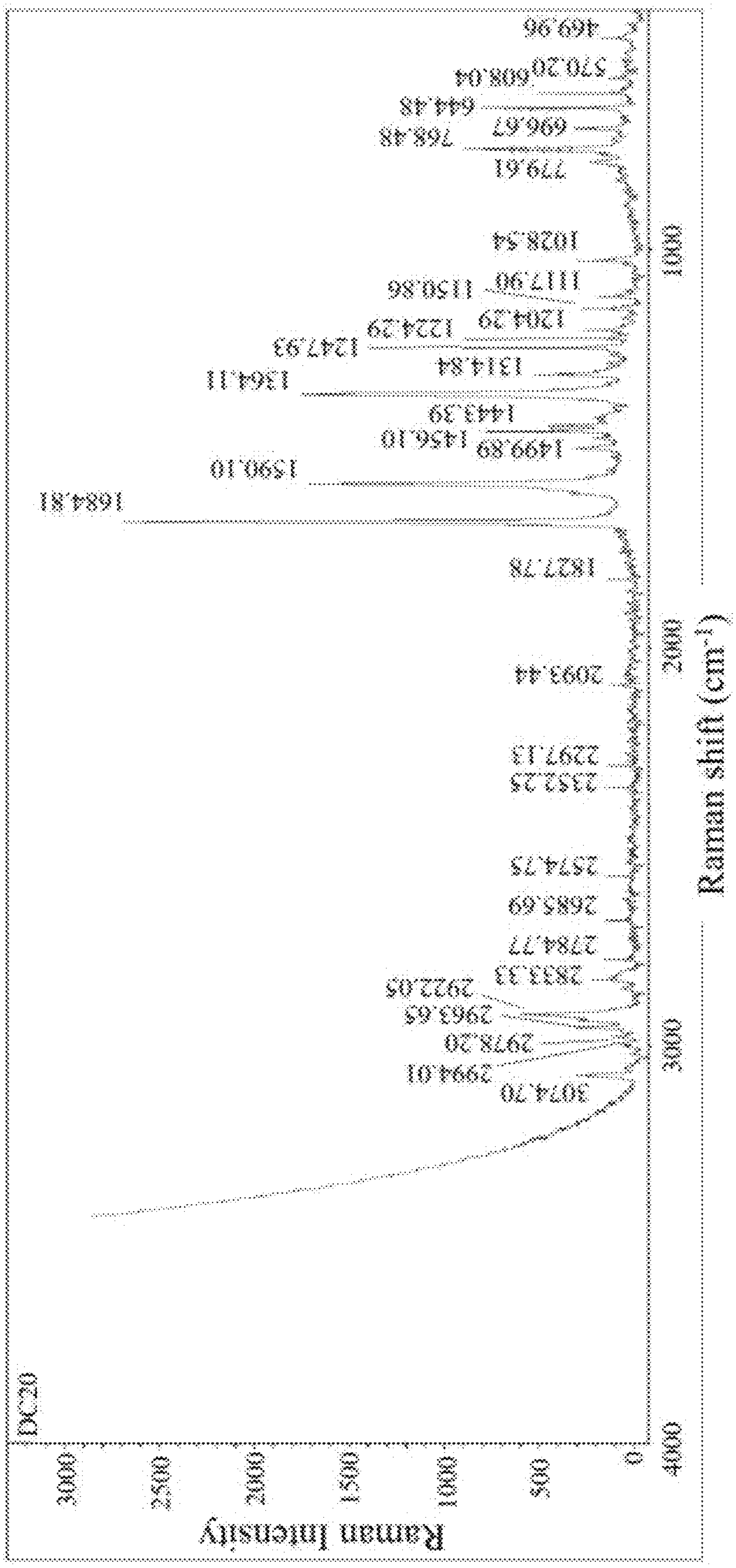
FIG. 7 is a Raman spectrum of Form A of Example 1.
Figure 8:
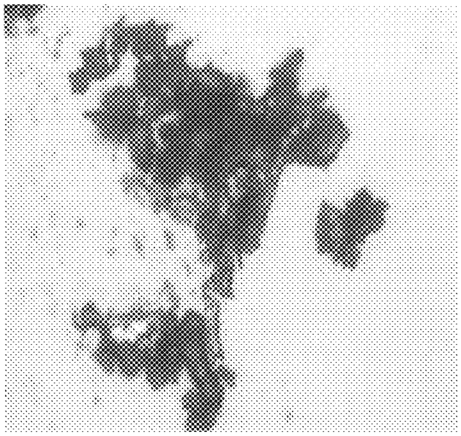
FIG. 8 is a polarizing microscope photograph of Form B of Example 1 (10*10).

In another preferred embodiment, the Form A has one or more features selected from the group consisting of:

1) the Form A has a TG pattern substantially as shown in FIG. 3;
2) the Form A has a DSC pattern substantially as shown in FIG. 4;
3) the Form A has a DVS pattern substantially as shown in FIG. 5;
4) the Form A has an IR pattern substantially as shown in FIG. 6; and/or
5) the Form A has a Raman pattern substantially as shown in FIG. 7.

Form B

Form B is an anhydrous and solvent-free crystalline form of the compound of formula I.

In another preferred embodiment, the X-ray powder diffraction pattern of the Form B has characteristic peaks at three or more 2θ values selected from the group consisting of 6.004±0.2°, 14.927±0.2°, 16.551±0.2°, 20.503±0.2° and 21.967±0.2°.

In another preferred embodiment, the X-ray powder diffraction pattern of the Form B has characteristic peaks at 2θ values substantially as shown in Table 2, wherein the 2θ value of each peak has an error margin of ±0.2°.

Figure 9:
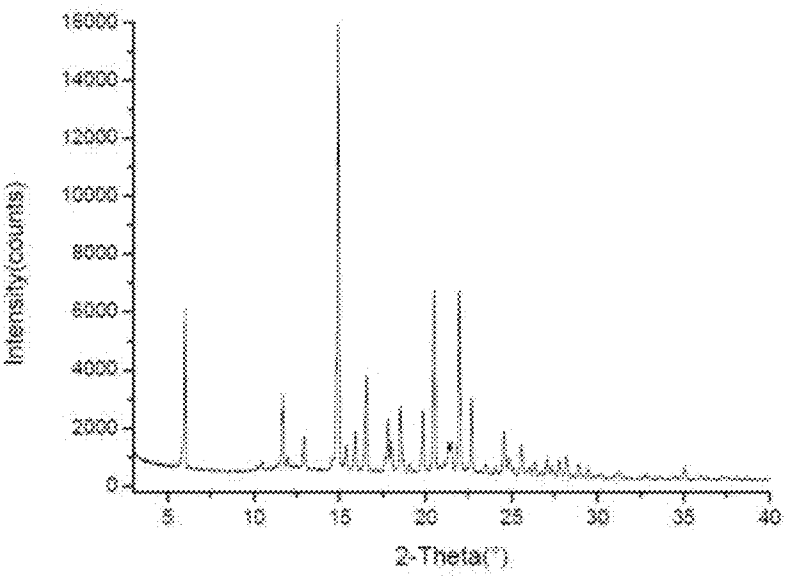
FIG. 9 is an XRD pattern of Form B of Example 1.
Figure 10:
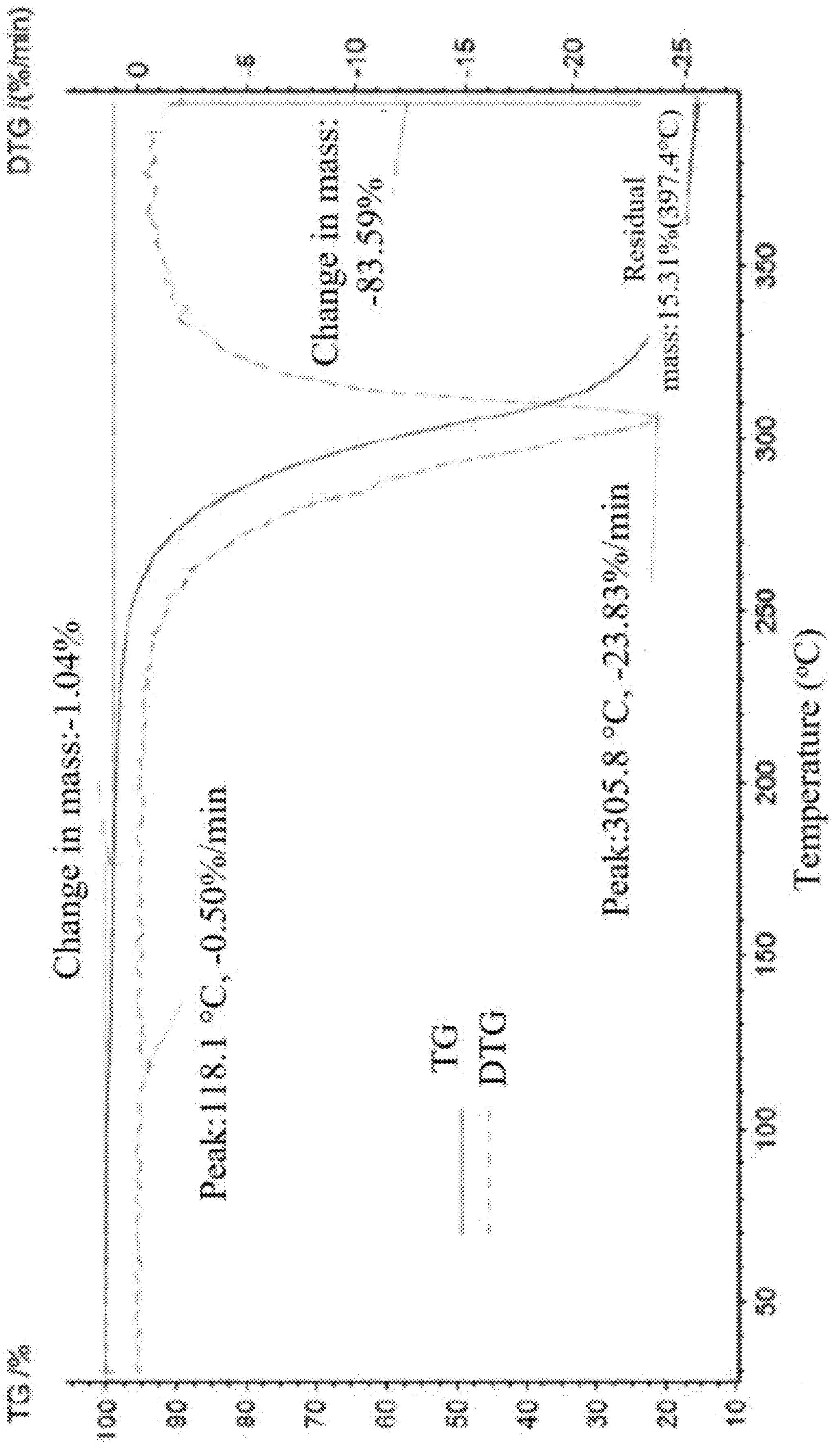
FIG. 10 is a TG pattern of the Form B of Example 1.
Figure 11:
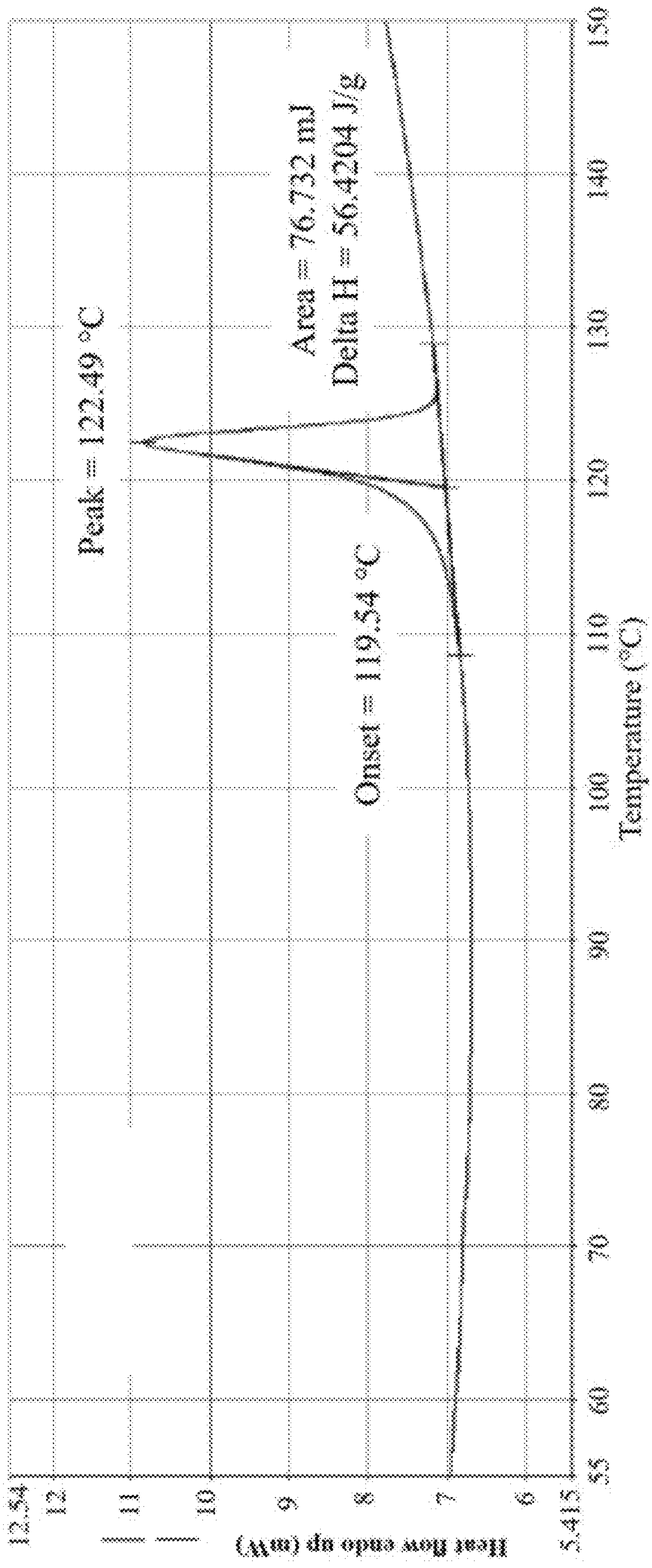
FIG. 11 is a differential scanning calorimetry (DSC) pattern of the Form B of Example 1.
Figure 12:
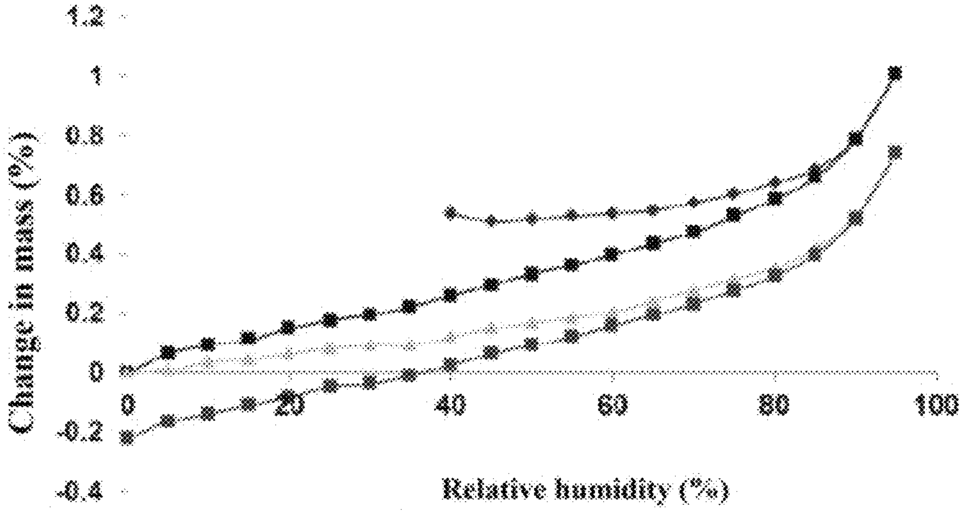
FIG. 12 is a dynamic vapor adsorption (DVS) pattern of Form B of Example 1.
Figure 13:
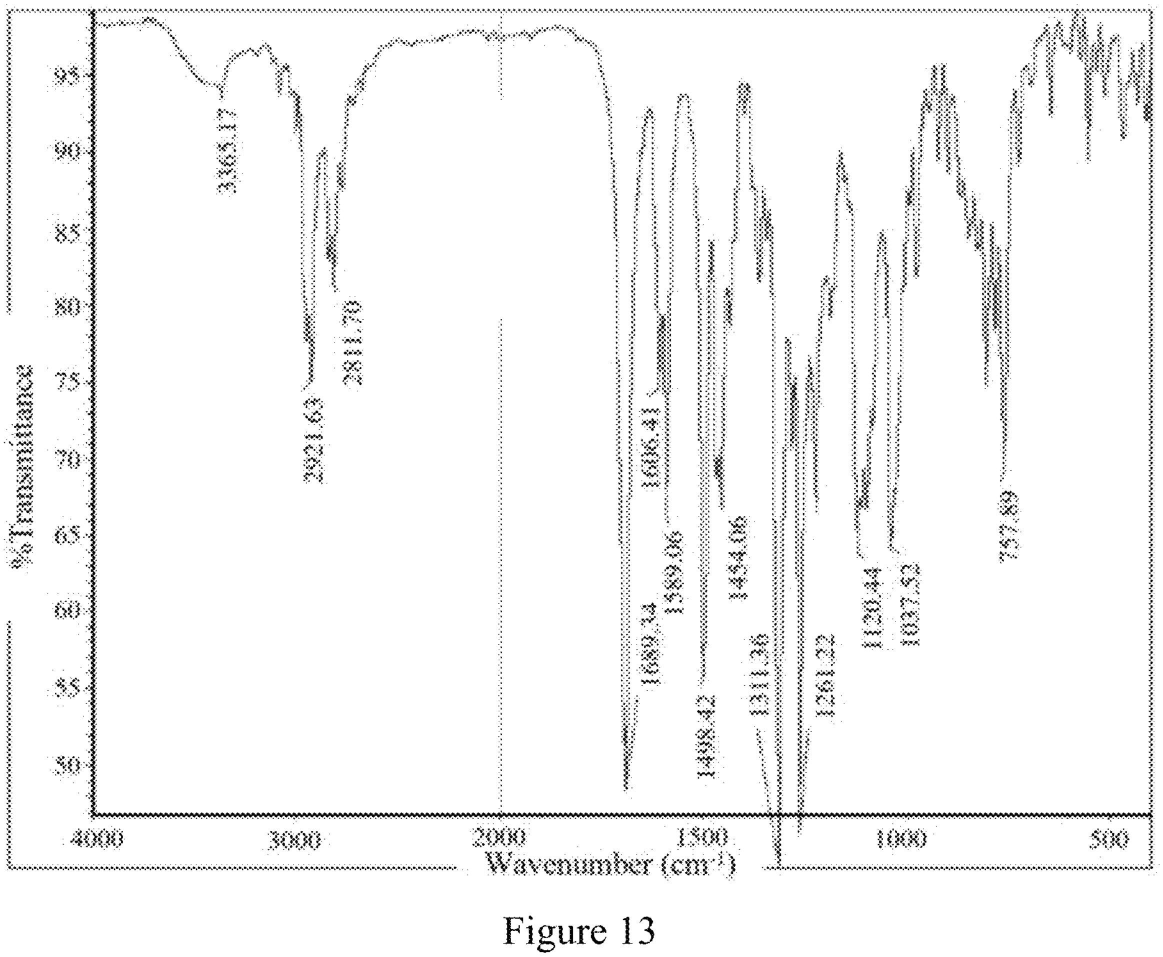
FIG. 13 is an infrared spectrum (IR) pattern of the Form B of Example 1.
Figure 14:
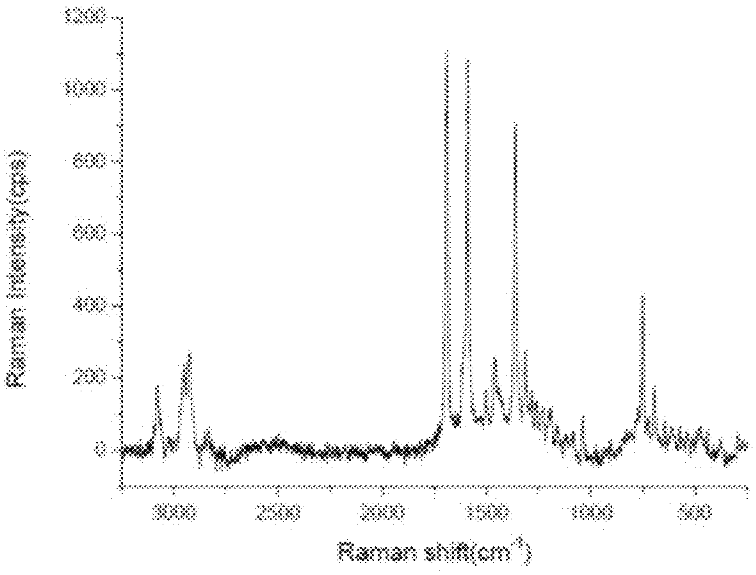
FIG. 14 is a Raman spectrum of Form B of Example 1.
Figure 15:
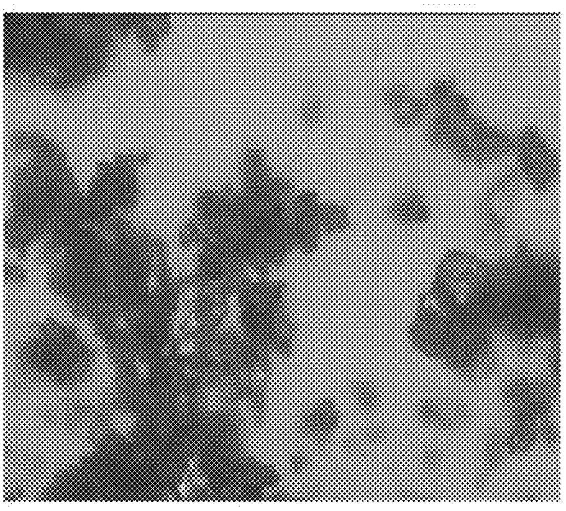
FIG. 15 is a polarizing microscope photograph of Form C of Example 1 (10*10).

In another preferred embodiment, the Form B has one or more features selected from the group consisting of:

1) the Form B has a TG pattern substantially as shown in FIG. 10;
2) the Form B has a DSC pattern substantially as shown in FIG. 11;
3) the Form B has a DVS pattern substantially as shown in FIG. 12;
4) the Form B has an IR pattern substantially as shown in FIG. 13;
5) the Form B has a Raman pattern substantially as shown in FIG. 14;
6) the Form B has an XRPD pattern substantially as shown in FIG. 9.

Form C

Form C is another anhydrous and solvent-free crystalline form of the compound of formula I.

In another preferred embodiment, the X-ray powder diffraction pattern of the Form C has characteristic peaks at three or more values of selected from the group consisting of 15.473±0.2°, 15.832±0.2°, 18.459±0.2°, 18.824±0.2°, 20.864±0.2°, 22.331±0.2°, and 24.374±0.2°.

Figure 16:
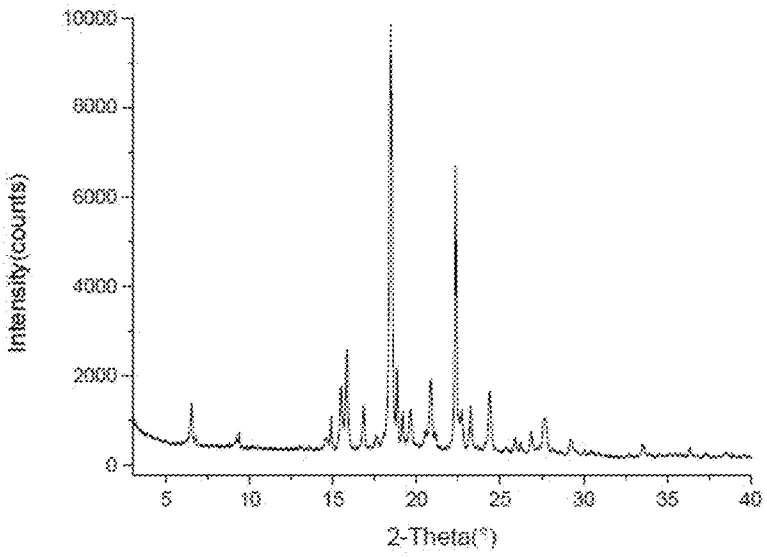
FIG. 16 is an XRD pattern of Form C of Example 1.
Figure 17:
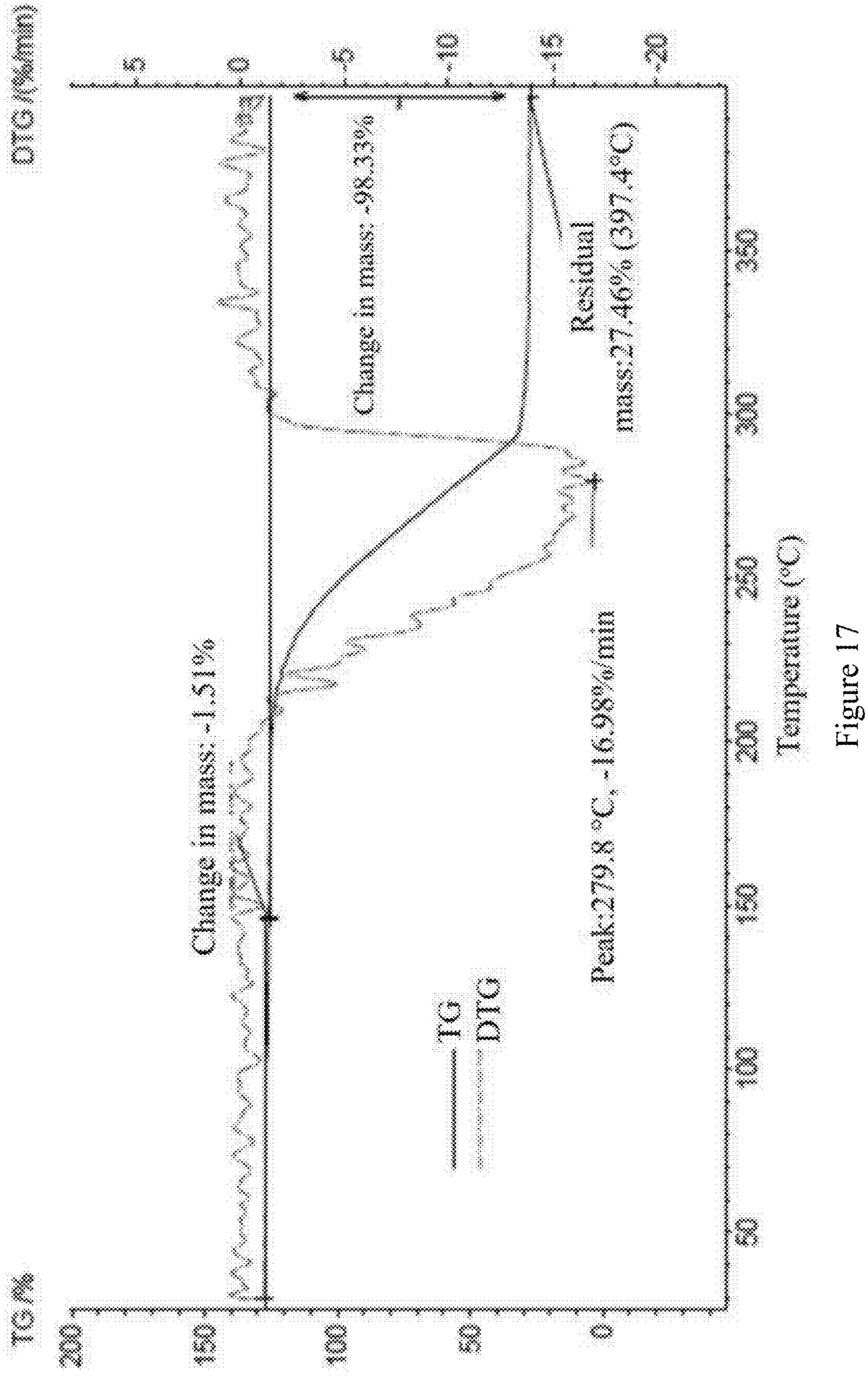
FIG. 17 is a TG pattern of the Form C of Example 1.
Figure 18:
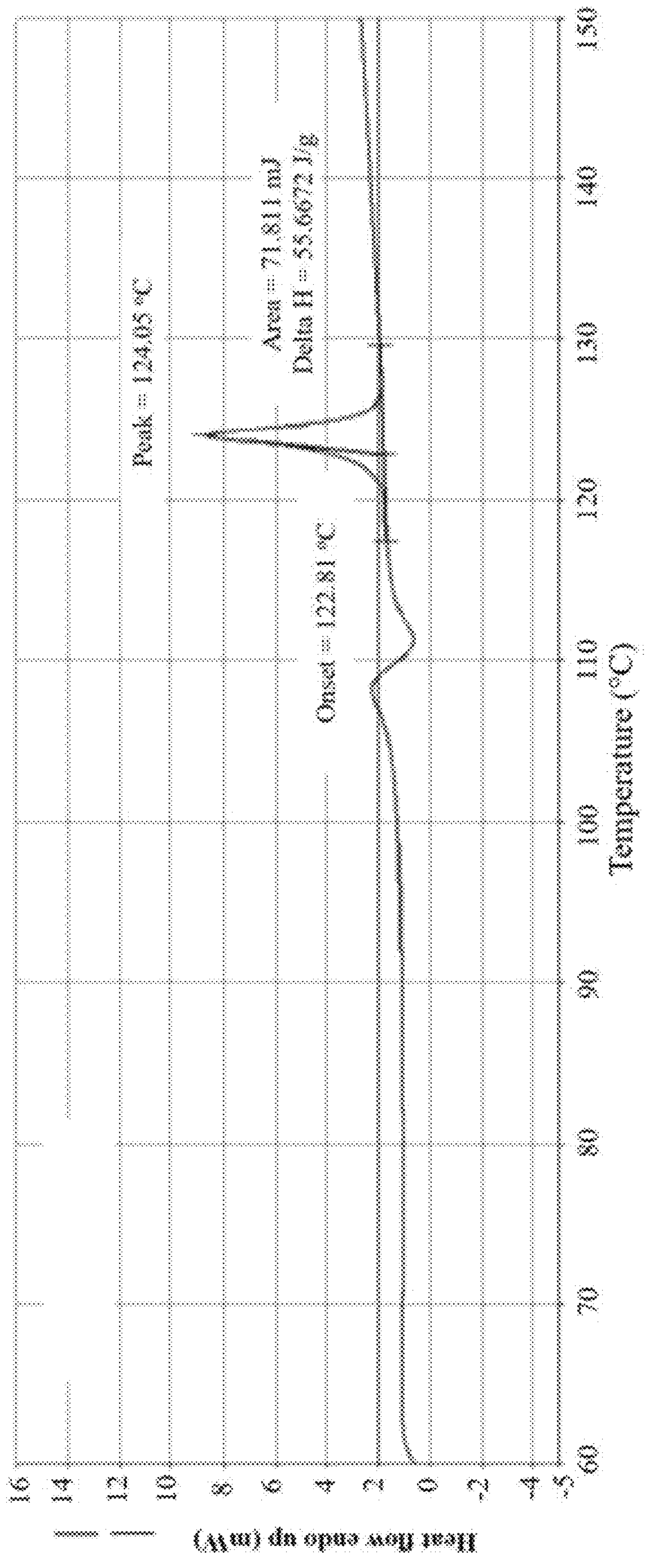
FIG. 18 is a differential scanning calorimetry (DSC) pattern of the Form C of Example 1.
Figure 19:
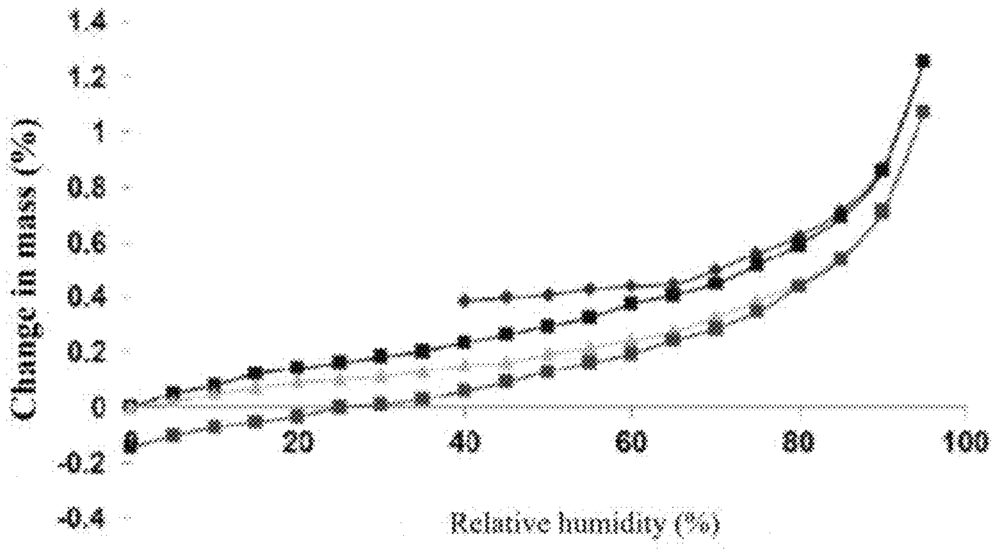
FIG. 19 is a dynamic vapor adsorption (DVS) pattern of Form C of Example 1.
Figure 20:
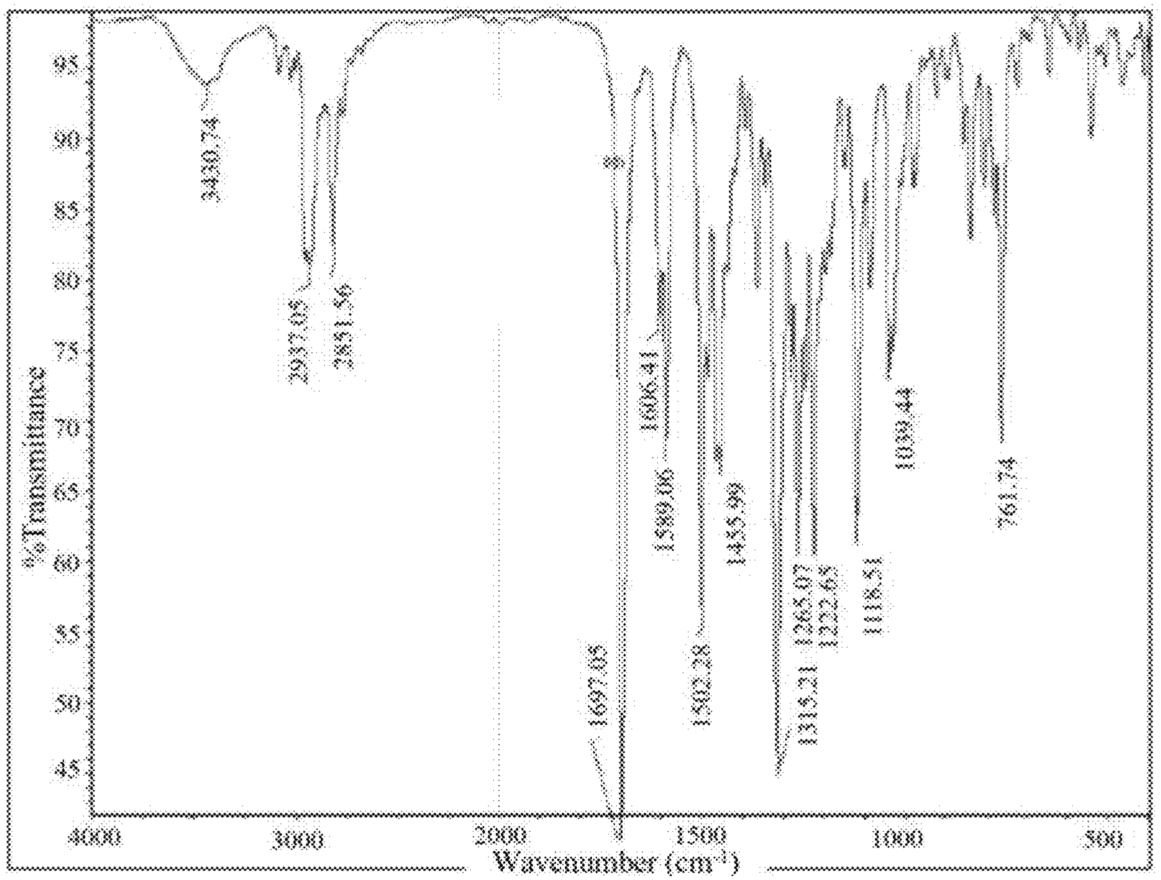
FIG. 20 is an infrared spectrum (IR) pattern of the Form C of Example 1.
Figure 21:
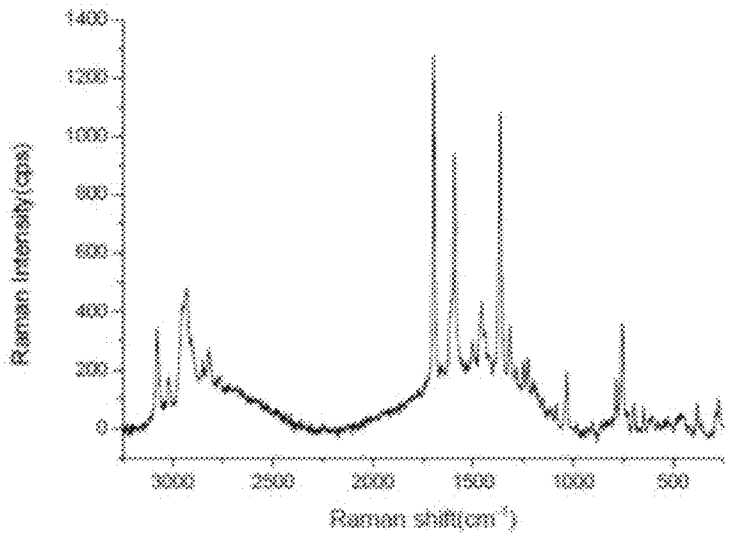
FIG. 21 is a Raman spectrum of the Form C of Example 1.

In another preferred embodiment, the Form C has one or more features selected from the group consisting of:

1) the Form C has a TG pattern substantially as shown in FIG. 17;
2) the Form C has a DSC pattern substantially as shown in FIG. 18;
3) the Form C has a DVS pattern substantially as shown in FIG. 19;
4) the Form C has an IR pattern substantially as shown in FIG. 20;
5) the Form C has a Raman pattern substantially as shown in FIG. 21; and/or
6) the Form C has an XRPD pattern substantially as shown in FIG. 16.

Crystalline Composition

The present invention also provides a crystalline composition comprising Form A, Form B, Form C according to the first aspect of the present invention, or any combination thereof.

In another preferred embodiment, the weight percentage of Form A is 60-99.999%, preferably 80-99.999%, more preferably 90-99.999%, based on the total weight of the crystalline composition.

In another preferred embodiment, the crystalline composition further comprises: a crystal of the compound of formula I other than Form A-C or an amorphous of compound of formula I.

Crystallization

Production-scale crystallization can be completed by manipulating the solution to let the solubility limit of the compound of interest being exceeded. This can be achieved by various methods, for example, dissolving a compound at a relatively high temperature, and then cooling the solution below the saturation limit. Or reducing the volume of liquid by boiling, atmospheric pressure evaporation, vacuum drying or other methods. The solubility of the compound of interest can be reduced by adding an anti-solvent or a solvent in which the compound has a lower solubility or a mixture of such solvents. Another alternative method is adjusting the pH to reduce solubility.

If the desired formation of the salt occurs at the same time as crystallization, and the solubility of the salt in the reaction medium is lower than the raw material, the addition of an appropriate acid or base can lead to direct crystallization of the desired salt. Similarly, in a medium where the final desired form is less soluble than the reactant, the completion of the synthesis reaction allows to directly crystallize the final product.

The optimization of crystallization may include seeding the desired form of crystalline in the crystallization medium. In addition, many crystallization methods use a combination of the above strategies. One embodiment is to dissolve the compound of interest in a solvent at an elevated temperature, followed by adding an appropriate volume of anti-solvent in a controlled manner so that the system is just below the saturation level. At this time, a seed crystal in required form (and the integrity of the seed crystal is maintained) can be added, then cooling the system to complete crystallization.

Preparation Method of Form A

The present invention provides a method for preparing the Form A of the compound of formula I, including a step of: suspending the compound of formula I in a first inert solvent, stirring, and filtering to obtain the Form A.

In another preferred embodiment, the first inert solvent is selected from the group consisting of alcohols, ethers, alkanes, and combinations thereof.

In the present invention, there are no particular limitation for the alcohols, ethers, and alkanes, and conventional materials in the art, or prepared by conventional methods, or purchased from the market.

In another preferred embodiment, the weight-volume ratio of the compound of formula I in the first inert solvent is 10-100 mg/mL, preferably 15-50 mg/mL, more preferably 20-40 mg/mL.

In another preferred embodiment, the alcohols is a C1-C10 alcohol, preferably a C1-C8 alcohol, more preferably a C1-C5 alcohol; more preferably, methanol, ethanol, n-propanol, isopropanol, n-butanol, isoamyl alcohol, or any combination thereof.

In another preferred embodiment, the ethers are C2-C10 ethers, preferably methyl tert-butyl ether, diethyl ether, or any combination thereof.

In another preferred embodiment, the alkane is a C5-C12 alkane, preferably n-pentane, n-hexane, or any combination thereof.

In another preferred embodiment, the stirring has one or more features selected from the group consisting of:

(1) the time for stirring is 12-48 h, preferably 18-36 h;

(2) the temperature for stirring is 25±5° C.

The Form A of the present invention can also be prepared by the following methods, including steps:

Dissolving the compound of formula I in a second inert solvent by heating, then cooling to crystallize to obtain the Form A.

In another preferred embodiment, the heating temperature for dissolution is 50-70° C., preferably 55-65° C.

In another preferred embodiment, the cooling temperature for crystallization is −10-10° C., preferably −4-0° C.

In another preferred embodiment, the second inert solvent is selected from the group consisting of alcohols, ethers, and combinations thereof.

In another preferred embodiment, the weight-volume ratio of the compound of formula I in the second inert solvent is from 1 to 100 mg/mL, preferably from 1 to 50 mg/mL, more preferably from 5 to 40 mg/mL.

In another preferred embodiment, the alcohols are C1-C10 alcohol, preferably a C1-C8 alcohol, more preferably a C1-C5 alcohol; preferably, methanol, ethanol, n-propanol, isopropanol, n-butanol, isoamyl alcohol, or any combination thereof.

In another preferred embodiment, the ethers are C2-C10 ethers, preferably methyl tert-butyl ether, diethyl ether, or any combination thereof.

The Form A of the present invention can also be prepared by the following method, including steps of: dissolving the compound of formula I in a third inert solvent, and then adding a poor solvent to crystallize to obtain the Form A.

Typically, the method is carried out at room temperature.

In another preferred embodiment, the third inert solvent (good solvent) is selected from the group consisting of ketones, esters, tetrahydrofuran, toluene, and combinations thereof.

In another preferred embodiment, the ketones are selected from the group consisting of methyl ethyl ketone, acetone, methyl isobutyl ketone, and combinations thereof.

In another preferred embodiment, the esters are selected from the group consisting of ethyl acetate, ethyl propionate, ethyl butyrate, ethyl valerate, ethyl caproate, and combinations thereof.

In another preferred embodiment, the poor solvent is selected from the group consisting of alkanes, ethers, and combinations thereof.

In another preferred embodiment, the alkanes are C5-C12 alkane, preferably n-pentane, n-hexane, petroleum ether, and combinations thereof.

In another preferred embodiment, the ethers are C2-C10 ethers, preferably methyl tert-butyl ether, diethyl ether, or any combination thereof.

Preferably, the raw material of the above-mentioned various preparation methods is the compound of formula I in an amorphous form.

Typically, the Form A obtained by the above-mentioned various preparation methods can be filtered, dried and the like by conventional means in the art as required.

Preferably, the filtration may be selected from, but not limited to, post-centrifuge filtration, pressure filtration, or vacuum filtration. The drying may be selected from, but is not limited to, vacuum drying or oven drying.

Pharmaceutical Compositions and Applications

The pharmaceutical composition of the present invention comprises a safe and effective amount of the crystalline form of the compound of formula I and a pharmaceutically acceptable carrier.

The "active ingredient" of the present invention refers to the compound of formula I according to the present invention, preferably, Form A-C of the present invention, and more preferably, Form A.

Typically, the weight percentage of Form A is 60-99.999%, preferably 80-99.999%, more preferably 90-99.999%, based on the total weight of the active ingredient.

The crystalline forms, crystalline compositions and pharmaceutical compositions of the present invention can be used to prevent and/or treat neurological diseases associated with acetylcholinesterase.

The crystalline forms, crystalline compositions and pharmaceutical compositions of the present invention can be used to prevent and/or treat neurodegenerative diseases.

The pharmacological activity of the compound of formula I is disclosed in WO 2014/063587, the whole content thereof is incorporated herein for all purpose.

Preferably, the neurodegenerative disease includes, but is not limited to, senile dementia (Alzheimer's disease), cerebrovascular dementia, attention deficit hyperactivity disorder, or any combination thereof.

The "safe and effective amount" refers to an amount of a compound that is sufficient to significantly improve the condition without causing serious side effects. Typically, the pharmaceutical composition contains 1-2000 mg of the crystalline form of the present invention/dose, and more preferably 10-500 mg of the compound of the present invention/dose. Preferably, the "one dose" is a capsule or a tablet.

"Pharmaceutically acceptable carrier" refers to one or more compatible solid or liquid fillers or gels suitable for human use and with sufficient purity and low enough toxicity. "Compatibility" herein refers to the ability of components of a composition to blend with the compounds of the invention and with each other, without significantly reducing the efficacy of the compounds. Examples of pharmaceutically acceptable carriers include cellulose and its derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oil (such as soybean oil, sesame oil, peanut oil, olive oil, etc.), polyols (such as propylene glycol, glycerin, mannitol, sorbitol, etc.), emulsifiers (such as Tween®), wetting agents (such as sodium dodecyl sulfate), colorants, flavoring agents, stabilizers, antioxidants, preservatives, pyrogen-free water, etc.

There are no particular limitations for the methods of administration of the compounds or pharmaceutical compositions of the present invention, and representative methods of administration include, but are not limited to, oral, rectal, parenteral (intravenous, intramuscular or subcutaneous), and topical administration.

Solid dosage forms for oral administration include capsules, tablets, pills, powders and granules. In these solid dosage forms, the crystalline form of the present invention is mixed with at least one conventional inert excipient (or carrier), such as sodium citrate or dicalcium phosphate, or mixed with the following ingredients: (a) filler or compatibilizer, such as starch, pregelatinized starch, lactose, microcrystalline cellulose, dextrin, mannitol, magnesium oxide, calcium sulfate, sucrose, glucose and silicic acid; (b) binders, e.g., hydroxymethyl cellulose, alginate, gelatin, polyvinylpyrrolidone, sucrose, and gum arabic; (c) humectants, e.g., glycerol; (d) disintegrants, e.g., agar, calcium carbonate, potato starch or tapioca starch, alginic acid, certain complex silicates, and sodium carbonate, carboxymethyl cellulose and salt thereof, croscarmellose and salt thereof, crospovidone, sodium carboxymethyl starch, low-substituted hydroxypropyl cellulose; (e) a slow-dissolving reagent, e.g., paraffin; (f) an absorption accelerator, e.g., a quaternary amine compound; (g) a wetting agent, e.g., cetyl alcohol and glyceryl monostearate; (h) an adsorbent, e.g., kaolin; and (i) a lubricant, e.g., talc, calcium stearate, magnesium stearate, solid polyethylene glycol, sodium dodecyl sulfate, and mixtures thereof. In capsules, tablets and pills, dosage forms may also contain buffers.

Preferably, the carrier is selected from the group consisting of a filler, a disintegrant, a lubricant, and combinations thereof.

Preferably, the filler is selected from the group consisting of pregelatinized starch, lactose, microcrystalline cellulose, dextrin, mannitol, magnesium oxide, calcium sulfate, and combinations thereof.

Preferably, the disintegrant is selected from the group consisting of carboxymethyl cellulose and salts thereof, cross-linked carboxymethyl cellulose and salts thereof, cross-linked povidone, sodium carboxymethyl starch, low-substituted hydroxypropyl cellulose, and combinations thereof.

Preferably, the lubricant is selected from the group consisting of magnesium stearate, calcium stearate, and combinations thereof.

Solid dosage forms such as tablets, sugar pills, capsules, pills and granules may be prepared using coating and shell materials such as casing and other materials well known in the art. They may comprise an opaque agent, and the release of Form A of the present invention in such a composition may be released in a delayed manner in a part of the digestive tract. Examples of embedding components that can be employed are polymeric substances and wax substances. If necessary, the Form A of the present invention may also form a microcapsule form with one or more of the excipients described above.

Liquid dosage forms for oral administration include pharmaceutically acceptable emulsions, solutions, suspensions, syrups or tinctures. In addition to Form A of the present invention, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil, or mixtures thereof.

In addition to these inert diluents, the composition may also contain auxiliaries such as wetting agents, emulsifiers, suspending agents, sweeteners, flavoring agents and flavors.

In addition to the crystalline forms of the present invention, the suspensions may comprise suspending agents, for example, ethoxylated isodecadanol, polyoxyethylene sorbitol and sorbitan esters, microcrystalline cellulose, aluminum methanol and agar, or mixtures thereof.

The composition for parenteral injection may comprise physiologically acceptable sterile aqueous or anhydrous solutions, dispersions, suspensions or emulsions, and sterile powders for redissolution into sterile injectable solutions or dispersions. Suitable aqueous and non-aqueous carriers, diluents, solvents, or excipients include water, ethanol, polyols, and suitable mixtures thereof.

The dosage forms of the crystalline forms of the present invention for topical administration include ointments, powder, patches, propellants and inhalants. The active ingredient is mixed under sterile conditions with a physiologically acceptable carrier and any preservatives, buffers or propellants as required.

The crystalline form of the present invention can be administered alone or in combination with other pharmaceutically acceptable compounds. For example, other cholinesterase inhibitors: such as tacrine, donepezil, huperzine A, galantamine, etc.; calcium antagonists: such as nimodipine, flunarizine hydrochloride, etc.; brain metabolism regulators: such as nicergoline, ammitriazine, piracetam, etc.; or neuroprotective agents: such as cerebrolysin.

The general range of the therapeutically effective dose of the crystalline form of the present invention may be about 1-2000 mg/day, about 10-about 1000 mg/day, about 10-about 500 mg/day, about 10-about 250 mg/day, about 10-about 100 mg/day, or about 10-about 50 mg/day. The therapeutically effective dose will be given in one or more units. However, it should be understood that the particular dose of the compound of the invention for any particular patient will depend on various factors, for example, age, sex, weight, general health condition, diet, individual response, time of administration, severity of the disease to be treated, activity of the particular compound to be administered, dosage form, mode of application, and concomitant drug. The therapeutic effectiveness of a given situation can be determined by routine experiments and is within the scope of clinician or physician's ability and judgment. In any case, the compound or composition will be administered in multiple doses based on the individual condition of the patient and in a manner that allows delivery of a therapeutically effective amount.

The main advantages of the invention include:

(1) The Form A-C of the compound of formula I of the present invention does not contain water or solvent, and has high stability and low hygroscopicity, and is very suitable for processing into medicine.

(2) The Form A-C of the compound of formula I of the present invention is uneasy to be raised, easy to be collected, and uneasy to cause waste, and it is helpful to protect the health of operators during the production of drugs such as packaging.

(3) The preparation method of the Form A-C of the compound of formula I of the present invention is simple and convenient, and is suitable for large-scale industrial production.

The present invention will be further explained below in conjunction with specific embodiments. It should be understood that these embodiments are only used to illustrate the present invention and not to limit the scope of the present invention. The experimental methods that do not indicate specific conditions in the following examples usually follow the conventional conditions, such as those described in Sambrook et al., Molecular Cloning: A Laboratory Manual (New York: Cold Spring Harbor Laboratory Press, 1989), or the conditions suggested by the manufacturer. Unless otherwise specified, percentages and parts are percentages by weight and parts by weight.

Detection Method

X-ray diffraction (XRD) is a structural analysis method for analyzing the spatial distribution of internal atoms on substance by using X-ray diffraction formed by crystals. When X-rays with a certain wavelength are irradiated on crystalline substances, the X-rays are scattered due to the regularly arranged atoms or ions in the crystalline, and the phase of the scattered X-rays is strengthened in certain directions, thus showing a unique diffraction phenomenon corresponding to the crystalline structure.

In the present invention, the test parameters of XRD are as follows: instrument model: Bruker D8advance; Target: Cu-$K_\alpha$ (40 kV, 40 mA); Distance from sample to detector: 30 cm; Scanning range: 3°~40° (2 theta value); Scanning step diameter: 0.1 s.

Thermo gravimetric analysis (TGA) is an analytical technique for determining the change of mass over temperature under the condition of program temperature control. Thermo gravimetric analysis can obtain the heat generated by the thermal change of the sample, and is suitable for checking the loss of crystal solvent or crystal water molecules in the crystalline substance or the process and value of sublimation and decomposition of the sample, and can also effectively distinguish whether the substance contains components of crystal solvent or crystal water.

In the present invention, the test parameters of TGA are as follows: instrument model: Netzsch TG 209F3; Crucible: alumina crucible; Temperature range: 30~400° C.; Scanning rate: 10 K/min; Purge gas: 25 mL/min; Protective gas: 15 mL/min.

Differential Scanning Calorimeter (DSC) is a technique that measures changes of the heat difference between a sample and an inert reference (alpha-$Al_2O_3$ is commonly used) over temperature by using a program to control heating or cooling. DSC detection is suitable for analyzing the molten decomposition state, mixed crystalline material state, crystal transfer material state and the like of a sample.

In the present invention, the test parameters of DSC are as follows: instrument model: Perkin Elmer DSC 8500; Crucible: aluminum crucible; Under nitrogen purge, scan from 50° C. to 280° C. at a heating rate of 10° C./min.

Raman spectroscopy (RM) is a method to study molecular vibrations based on the Raman effect. In contrast to infrared absorption spectroscopy, Raman spectroscopy studies the frequency of scattered light generated by the interaction of molecules and light. Generally, non-polar groups with insignificant infrared absorption have obvious Raman absorption.

In the present invention, the test parameters of RM are as follows: instrument model: Thermo DXR Raman Microscope confocal micro Raman spectrometer; Laser wavelength: 532 nm; Exposure time: 1.0 sec; Exposure times: 10.

Infra-red Spectrometry (IR) is the earliest analytical method for recognition and identification of crystalline substances. Because the electrical environment of covalent bonds of different crystalline forms is different, the strength of covalent bonds may also change, and the change of covalent bond strength will inevitably lead to IR spectra of different Crystalline forms being different.

In the present invention, the test parameters of IR are as follows: instrument model: Nicolet 6700 Fourier transform infrared spectrometer; Single point ATR method with a resolution of 4.0 $cm^{-1}$.

Dynamic Vapor Sorption (DVS) test/Hygroscopicity test is a rapid measurement of the increase and loss of sample moisture caused by a flowing carrier gas with a set relative humidity (RH). The hygroscopicity of the sample is then determined by measuring the increase/decrease in the mass of the material to detect the adsorption/desorption of water vapor on a high-sensitivity, high-stability digital microbalance in a self-suspended state.

In the present invention, the test parameters of DVS are as follows: instrument model: SMS DVS Intrinsic; measurement temperature 25° C., 0-95% RH.

Polarizing Microscope

In the present invention, the type of polarizing microscope instrument: XPV-400E.

Example 1

Preparation of Form A of 2-((1-(2-fluorobenzyl)-4-fluoropiperidin-4-yl) methylene)-5, 6-dimethoxy-2, 3-dihydro-1-indanone 25 mg of 2-((1-(2-fluorobenzyl)-4-fluoropiperidin-4-yl) methylene)-5, 6-dimethoxy-2, 3-dihydro-1-indanone was dissolved in 1 mL of ethanol and stirred at room temperature at 25° C., equilibrated for at least 24 h. The resulting solid material was filtered and placed in a vacuum drying oven, dried in vacuum to give Form A of 2-(1-(2-fluorobenzyl)-4-fluoropiperidin-4-yl)methylene)-5,6-Dimethoxy-2, 3-dihydro-1-indanone.

Form A prepared in Example 1 was subjected to tests such as polarizing microscope imaging, XRPD, TGA, DSC, DVS, IR and Raman, and the characterization results were shown in FIGS. 1 to 7.

FIG. 1 is a polarizing microscope photograph of Form A. It can be seen from FIG. 1 that Form A is a columnar crystal.

FIG. 2 is an XRPD pattern of Form A (the peak table is as shown in Table 1).

TABLE 1

X-ray powder diffraction peaks of Form A

| 2-Theta | Height |
|---|---|
| 6.006 | 1450 |
| 6.809 | 1575 |
| 8.537 | 697 |
| 8.777 | 1391 |
| 10.529 | 454 |
| 11.685 | 735 |
| 12.223 | 466 |
| 12.73 | 468 |
| 12.922 | 548 |
| 13.204 | 574 |
| 13.612 | 941 |
| 14.672 | 1324 |
| 14.914 | 5292 |
| 15.593 | 3535 |
| 15.95 | 1312 |
| 16.539 | 984 |
| 17.12 | 1568 |
| 17.617 | 6553 |
| 18.022 | 2756 |
| 18.578 | 1117 |
| 19.123 | 1211 |
| 19.525 | 2121 |
| 20.028 | 1816 |
| 20.506 | 1470 |
| 20.806 | 6144 |
| 21.463 | 1625 |
| 21.99 | 1513 |
| 22.637 | 906 |
| 23.692 | 455 |
| 24.135 | 537 |
| 24.419 | 783 |
| 24.917 | 775 |
| 25.582 | 627 |
| 25.918 | 1496 |
| 26.546 | 483 |
| 26.782 | 489 |
| 27.087 | 425 |
| 27.464 | 455 |
| 27.845 | 487 |
| 28.606 | 950 |
| 29.792 | 652 |
| 31.532 | 466 |

TABLE 1-continued

X-ray powder diffraction peaks of Form A

| 2-Theta | Height |
|---|---|
| 32.038 | 287 |
| 33.171 | 283 |
| 33.564 | 340 |
| 34.56 | 476 |
| 35.082 | 359 |
| 36.506 | 252 |
| 37.569 | 375 |
| 38.015 | 268 |
| 38.712 | 399 |
| 39.237 | 242 |

FIG. 3 is a TG pattern of Form A. It can be seen from FIG. 3 that Form A has no weight loss before the decomposition of the compound, indicating that Form A does not contain water or other solvents.

FIG. 4 is a differential scanning calorimeter (DSC) pattern of Form A. It can be seen from FIG. 4 that the DSC corresponding to Form A shows two obvious melting peaks that cannot be completely separated at a oneset of about 120° C. (Peak is about 123.5° C.). The temperature at which Form A starts to melt is at 120° C.

FIG. 5 is a dynamic vapor adsorption (DVS) pattern of Form A. It can be seen from FIG. 5 that the change in hygroscopicity of Form A within the range of 0-95% relative humidity is very small, is about 0.6%, and a small change in weight indicates that the Form A has low hygroscopicity.

FIG. 6 is an infrared spectrum (IR) pattern of Form A. It can be seen from FIG. 6 that the Form A has characteristic absorption peaks at 2952 $cm^{-1}$, 2922 $cm^{-1}$, 2817 $cm^{-1}$, 1693 $cm^{-1}$, 1604 $cm^{-1}$, 1589 $cm^{-1}$, 1498 $cm^{-1}$, 1454 $cm^{-1}$, 1365 $cm^{-1}$, 1315 $cm^{-1}$, 1265 $cm^{-1}$, 1118 $cm^{-1}$, 1039 $cm^{-1}$, and 762 $cm^{-1}$.

FIG. 7 is a Raman spectrum of Form A. It can be seen from FIG. 7 that Form A has characteristic absorption peaks at 748.48 $cm^{-1}$, 1314.84 $cm^{-1}$, 1364.11 $cm^{-1}$, 1443.39 $cm^{-1}$, 1456.10 $cm^{-1}$, 1590.10 $cm^{-1}$, 1684.81 $cm^{-1}$, 2922.05 $cm^{-1}$ and 2953.62 $cm^{-1}$.

Example 2

Preparation of Form A of 2-((1-(2-fluorobenzyl)-4-fluoropiperidin-4-yl) methylene)-5, 6-dimethoxy-2, 3-dihydro-1-indanone 25 mg of 2-((1-(2-fluorobenzyl)-4-fluoropiperidin-4-yl) methylene)-5, 6-dimethoxy-2, 3-dihydro-1-indanone was dissolved in 1 mL of isopropanol and stirred at room temperature at 25° C., equilibrated for at least 24 h. The resulting solid material was filtered and placed in a vacuum drying oven, dried under vacuum to give Form A of 2-(1-(2-fluorobenzyl)-4-fluoropiperidin-4-yl) methylene)-5,6-Dimethoxy-2, 3-dihydro-1-indanone.

The XRPD result of the resulting product is substantially the same as that of Example 1.

Example 3

Preparation of Form A of 2-((1-(2-fluorobenzyl)-4-fluoropiperidin-4-yl) methylene)-5, 6-dimethoxy-2, 3-dihydro-1-indanone 25 mg of 2-((1-(2-fluorobenzyl)-4-fluoropiperidin-4-yl) methylene)-5, 6-dimethoxy-2, 3-dihydro-1-indanone was dissolved in 1 mL of n-hexane and stirred at room temperature at 25° C., equilibrated for at least 24 h. The resulting solid material was filtered and placed in a vacuum drying oven. dried under vacuum to give Form A of 2-(1-(2-fluorobenzyl)-4-fluoropiperidin-4-yl) methylene)-5,6-Dimethoxy-2, 3-dihydro-1-indanone.

The XRPD result of the resulting product is substantially the same as that of Example 1.

Example 4

Preparation of Form A of 2-((1-(2-fluorobenzyl)-4-fluoropiperidin-4-yl) methylene)-5, 6-dimethoxy-2, 3-dihydro-1-indanone 25 mg of 2-((1-(2-fluorobenzyl)-4-fluoropiperidin-4-yl) methylene)-5, 6-dimethoxy-2, 3-dihydro-1-indanone was dissolved in 1 mL of methyl tert-butyl ether and stirred at room temperature at 25° C., equilibrated for at least 24 h. The resulting solid material was filtered and placed in a vacuum drying oven, dried under vacuum to give Form A of 2-(1-(2-fluorobenzyl)-4-fluoropiperidin-4-yl) methylene)-5, 6-Dimethoxy-2, 3-dihydro-1-indanone.

The XRPD result of the resulting product is substantially the same as that of Example 1.

Example 5

Preparation of Form A of 2-((1-(2-fluorobenzyl)-4-fluoropiperidin-4-yl) methylene)-5, 6-dimethoxy-2, 3-dihydro-1-indanone About 20 mg of 2-((1-(2-fluorobenzyl)-4-fluoropiperidin-4-yl) methylene)-5, 6-dimethoxy-2, 3-dihydro-1-indanone was taken and dissolved in 2 ml of ethanol, and heated to 60° C. with stirring until completely dissolved. Then the solution was placed in an ice bath while stirring continuously. If there is no precipitation within 4 hours, then the solution was frozen and stored at −4° C. overnight. After filtration, the precipitate was collected and dried to obtain Form A.

The XRPD result of the resulting product is substantially the same as that of Example 1.

Example 6

Preparation of Form A of 2-((1-(2-fluorobenzyl)-4-fluoropiperidin-4-yl) methylene)-5, 6-dimethoxy-2, 3-dihydro-1-indanone About 20 mg of 2-((1-(2-fluorobenzyl)-4-fluoropiperidin-4-yl) methylene)-5, 6-dimethoxy-2, 3-dihydro-1-indanone was taken and dissolved in 2 ml of isopropanol, and heated to 60° C. with stirring until completely dissolved. Then the solution was placed in an ice bath while stirring continuously. If there is no precipitation within 4 hours, then the solution was frozen and stored at −4° C. overnight. After filtration, the precipitate was collected and dried to obtain Form A.

The XRPD result of the resulting product is substantially the same as that of Example 1.

Example 7

Preparation of Form A of 2-((1-(2-fluorobenzyl)-4-fluoropiperidin-4-yl) methylene)-5, 6-dimethoxy-2, 3-dihydro-1-indanone About 20 mg of 2-((1-(2-fluorobenzyl)-4-fluoropiperidin-4-yl) methylene)-5, 6-dimethoxy-2, 3-dihydro-1-indanone was taken and dissolved in 2 ml of methyl tert-butyl ether, and heated to 60° C. with stirring until completely dissolved. Then the solution was placed in an ice bath while stirring continuously. If there is no precipitation within 4 hours, then the solution was frozen and stored at −4° C. overnight. After filtration, the precipitate was collected and dried to obtain Form A.

The XRPD result of the resulting product is substantially the same as that of Example 1.

Example 8

Preparation of Form A of 2-((1-(2-fluorobenzyl)-4-fluoropiperidin-4-yl) methylene)-5, 6-dimethoxy-2, 3-dihydro-1-indanone About 25 mg of 2-((1-(2-fluorobenzyl)-4-fluoropiperidin-4-yl) methylene)-5, 6-dimethoxy-2, 3-dihydro-1-indanone was taken and dissolved in 0.5 ml of methyl ethyl ketone (good solvent), and then 4 ml of n-pentane (anti-solvent) was slowly added along the wall to precipitate. After filtration, the precipitate was collected and dried to obtain Form A.

The XRPD result of the resulting product is substantially the same as that of Example 1.

Example 9

Preparation of Form A of 2-((1-(2-fluorobenzyl)-4-fluoropiperidin-4-yl) methylene)-5, 6-dimethoxy-2, 3-dihydro-1-indanone About 25 mg of 2-((1-(2-fluorobenzyl)-4-fluoropiperidin-4-yl) methylene)-5, 6-dimethoxy-2, 3-dihydro-1-indanone was taken and dissolved in 0.5 ml of ethyl acetate (good solvent), and then 4 ml of n-hexane (anti-solvent) was slowly added along the wall to precipitate. After filtration, the precipitate was collected and dried to obtain Form A.

The XRPD result of the resulting product is substantially the same as that of Example 1.

Example 10

Preparation of Form B of 2-((1-(2-fluorobenzyl)-4-fluoropiperidin-4-yl) methylene)-5, 6-dimethoxy-2, 3-dihydro-1-indanone An appropriate amount of 2-((1-(2-fluorobenzyl)-4-fluoropiperidin-4-yl) methylene)-5, 6-dimethoxy-2, 3-dihydro-1-indanone was taken and dissolved in toluene, and then slowly volatilized to dryness at 50° C. Solids was collected to obtain Form B.

Form B prepared in Example 10 was subjected to tests such as polarizing microscope imaging, XRPD, TGA, DSC, DVS, IR and Raman, and the characterization results were shown in FIGS. 8 to 14.

TABLE 2

X-ray powder diffraction peaks of Form B

| 2-Theta | Height |
|---|---|
| 6.004 | 6149 |
| 10.217 | 715 |
| 10.503 | 874 |
| 11.7 | 3189 |
| 11.968 | 1020 |

TABLE 2-continued

| X-ray powder diffraction peaks of Form B | |
|---|---|
| 2-Theta | Height |
| 12.493 | 750 |
| 12.94 | 1748 |
| 14.59 | 991 |
| 14.927 | 16027 |
| 15.371 | 1448 |
| 15.898 | 1893 |
| 16.551 | 3800 |
| 17.816 | 2339 |
| 18 | 1611 |
| 18.54 | 2783 |
| 19.063 | 811 |
| 19.843 | 2633 |
| 20.503 | 6724 |
| 20.819 | 690 |
| 21.069 | 844 |
| 21.47 | 1552 |
| 21.967 | 6736 |
| 22.653 | 3042 |
| 23.477 | 825 |
| 24.075 | 676 |
| 24.575 | 1896 |
| 24.838 | 975 |
| 25.113 | 618 |
| 25.562 | 1430 |
| 26.019 | 694 |
| 26.355 | 870 |
| 26.739 | 486 |
| 27.062 | 1000 |
| 27.343 | 699 |
| 27.782 | 918 |
| 28.206 | 1033 |
| 28.903 | 811 |
| 29.45 | 651 |
| 30.215 | 406 |
| 31.254 | 482 |
| 32.776 | 410 |
| 33.685 | 325 |
| 34.524 | 347 |
| 35.062 | 665 |
| 36.025 | 356 |
| 36.433 | 314 |
| 37.332 | 342 |
| 37.636 | 312 |
| 38.046 | 292 |
| 38.635 | 309 |

It can be seen from FIGS. 8 to 14, Form B does not contain water or other solvents and is a granular crystal. The melting temperature is 122.49° C. and the decomposition temperature is 250° C. the hygroscopicity thereof is low and the humidity change is 1% within the conventional storage humidity range.

In addition, volatilization in the following solvent obtains Form B: methanol:methyl isobutyl ketone=1:1; acetone: MIBK=1:1; THF:toluene=1:1; toluene:ethanol=2:1; toluene:water:methanol=2:2:1.

Example 11

Preparation of Form C of 2-((1-(2-fluorobenzyl)-4-fluoropiperidin-4-yl) methylene)-5, 6-dimethoxy-2, 3-dihydro-1-indanone An appropriate amount of 2-((1-(2-fluorobenzyl)-4-fluoropiperidin-4-yl) methylene)-5, 6-dimethoxy-2, 3-dihydro-1-indanone was taken and dissolved in a mixed solvent of ethyl acetate:water:methanol=2:2:1, and then slowly volatilized to dryness at 25° C. Solids was collected to obtain Form C.

TABLE 3

| X-ray powder diffraction peaks of Form C | |
|---|---|
| 2-Theta | Height |
| 6.527 | 1423 |
| 6.792 | 648 |
| 8.764 | 484 |
| 9.214 | 649 |
| 9.391 | 730 |
| 10.088 | 446 |
| 13.005 | 447 |
| 14.534 | 629 |
| 14.891 | 1107 |
| 15.473 | 1766 |
| 15.832 | 2605 |
| 16.833 | 1356 |
| 17.597 | 666 |
| 18.022 | 705 |
| 18.459 | 9888 |
| 18.824 | 2211 |
| 19.164 | 1217 |
| 19.625 | 1248 |
| 20.527 | 809 |
| 20.864 | 1920 |
| 21.106 | 773 |
| 22.331 | 6719 |
| 22.709 | 1230 |
| 23.231 | 1339 |
| 23.685 | 423 |
| 24.374 | 1659 |
| 25.375 | 422 |
| 25.882 | 621 |
| 26.222 | 543 |
| 26.863 | 770 |
| 27.703 | 1066 |
| 28.126 | 379 |
| 29.248 | 591 |
| 29.639 | 325 |
| 30.032 | 367 |
| 30.489 | 328 |
| 30.912 | 298 |
| 32.722 | 265 |
| 33.505 | 490 |
| 34.521 | 259 |
| 35.142 | 261 |
| 36.349 | 396 |
| 36.707 | 241 |
| 37.345 | 264 |
| 38.472 | 306 |
| 39.637 | 262 |

Form C prepared in Example 11 was subjected to tests such as polarizing microscope imaging, XRPD, TGA, DSC, DVS, IR and Raman, and the characterization results were shown in FIGS. 15 to 21.

It can be seen from FIGS. 15-21 that the Form C is a metastable crystal, does not contain water or other solvents, and is granular crystal; the melting temperature is 124.05° C., and the decomposition temperature is 210° C.; hygroscopicity thereof is low and the humidity change is 1.2% within the conventional storage humidity range.

In addition, volatilization in the following solvent also obtain Form C: methanol:toluene=1:2.

Example 12

Crystal Transformation Experiment

Form A and Form B were mixed in equal amounts, and mixed in EA/Hep(1:1) to give a suspension, and XRPD test is performed after stirring at normal temperature (25° C.) for three days.

TABLE 4

| Raw material | Results |
|---|---|
| Form A 5 mg + Form B 5 mg | Form A |

Form C is a metastable crystalline and transfers to Form B.

It can be seen from the above that the stability order of the three crystalline forms is Form A>Form B>Form C.

Example 13

Solubility Experiment

The solubility of each crystalline form was determined in water, the results are shown in Table 5:

TABLE 5

| Results of Solubility experiment (mg/mL) | | |
|---|---|---|
| | Form A | Form B |
| pH 2.01 | 12.35 | 20.5 |
| pH 4.59 | 1.86 | 2.79 |
| pH 6.74 | 0.14 | 0.18 |
| Pure water | 0.14 | 0.0089 |

Wherein, Form C becomes Form B after being transformed, so the solubility of Form C is the same as Form B.

It can be seen from Table 5 that the solubility of each crystalline form in pure water is very small, and the solubility increases as the pH decreases. Surprisingly, under acidic conditions, the solubility of Form B is significantly greater than that of Form A, and can be used to prepare aqueous solutions with higher concentrations.

Example 14

Pharmaceutical Composition

- Form A of 2-((1-(2-fluorobenzyl)-4-fluoropiperidin-4-yl) methylene)-5, 6-dimethoxy-2, 3-dihydro-1-indanone (prepared according to the method of Example 1) 2.0 g
- Pre-gelatinized starch 22.0 g
- Microcrystalline cellulose 100.0 g
- Low substituted hydroxypropyl cellulose 5.0 g
- Magnesium stearate 1.0 g According to the conventional method, the above substances was mixed evenly, then pressed into tablet to obtain 1000 tablets.

In summary, the present invention provides Form A-C of the compound of formula I, all of them are water-free or solvent-free crystalline form, have very low hygroscopicity, and are very suitable for processing into medicine. Form A-C of the compound of formula I of the present invention is uneasy to be raised, but easy to be collected, is not easy to waste, and helps to protect the health of operators during the production of drugs such as packaging.

All documents referred to in the present invention are incorporated by reference herein as if each document is individually incorporated by reference. Further, it should be understood that upon reading the above teaching of the present invention, various modifications or modifications may be made to the present invention by those skilled in the art, and those equivalents also fall within the scope defined by the appended claims of the present application.

The invention claimed is:

1. A crystalline form of a compound of formula I, wherein the crystalline form is selected from the group consisting of: Form A, Form B and Form C,

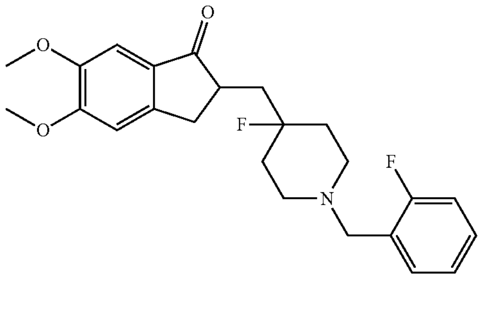

I

;

wherein Form A has an X-ray powder diffraction pattern with characteristic peaks at three or more 2θ values selected from the group consisting of 14.914±0.2°, 15.593±0.2°, 17.617±0.2°, 18.022±0.2°, 19.525±0.2°, and 20.806±0.2°;

Form B has an X-ray powder diffraction pattern with characteristic peaks at three or more 2θ values selected from the group consisting of 6.004±0.2°, 14.927±0.2°, 16.551±0.2°, 20.503±0.2° and 21.967±0.2°; and Form C has an X-ray powder diffraction pattern with characteristic peaks at three or more 2θ values selected from the group consisting of 15.473±0.2°, 15.832±0.2°, 18.459±0.2°, 18.824±0.2°, 20.864±0.2°, 22.331±0.2°, and 24.374±0.2°.

2. The crystalline form according to claim 1, wherein the X-ray powder diffraction pattern of the Form A has characteristic peaks at 2θ values 14.914±0.2°, 15.593±0.2°, 17.617±0.2°, 18.022±0.2°, 19.525±0.2°, and 20.806±0.2°.

3. The crystalline form according to claim 1, wherein the X-ray powder diffraction pattern of the Form B has characteristic peaks at 2θ values 6.004±0.2°, 14.927±0.2°, 16.551±0.2°, 20.503±0.2° and 21.967±0.2°.

4. The crystalline form according to claim 1, wherein the X-ray powder diffraction pattern of the Form C has characteristic peaks at 2θ values 15.473±0.2°, 15.832±0.2°, 18.459±0.2°, 18.824±0.2°, 20.864±0.2°, 22.331±0.2°, and 24.374±0.2°.

5. A method for preparing the crystalline form according to claim 1, comprising providing a solution of the compound of formula I in an inert solvent, and volatilizing the solvent at 10-60° C. to obtain the Form B; wherein the inert solvent is selected from the group consisting of toluene, a mixed solvent of methanol and methyl isobutyl ketone, a mixed solvent of acetone and methyl isobutyl ketone, a mixed solvent of THF and toluene, a mixed solvent of toluene and ethanol, and a mixed solvent of toluene, water and methanol.

6. A method for preparing the crystalline form according to claim 1, wherein the method comprises suspending the compound of formula I in an inert solvent, stirring at 25±5° C., and filtering to obtain the Form A, wherein the inert solvent is selected from the group consisting of C1-C5 alcohols, n-pentane, n-hexane, methyl tert-butyl ether, and diethyl ether.

7. A method for preparing the crystalline form according to claim 1, wherein the method comprises dissolving the compound of formula I in an inert solvent by heating, then cooling to −10° C. to 10° C. and crystallizing to obtain the Form A, wherein the inert solvent is selected from the group consisting of: C1-C5 alcohol, methyl tert-butyl ether, and diethyl ether.

8. A method for preparing the crystalline form according to claim 1, wherein the method comprises dissolving the compound of formula I in an inert solvent, then adding an anti-solvent to crystallize to obtain the Form A, wherein the inert solvent is selected from the group consisting of: methyl ethyl ketone, acetone, methyl isobutyl ketone, ethyl acetate, ethyl propionate, ethyl butyrate, ethyl valerate, and ethyl caproate and the anti-solvent is selected from the group consisting of: n-pentane, n-hexane, petroleum ether, and combinations thereof.

9. A method for treating a neurological disease associated with acetylcholinesterase, comprising administering to a subject in need thereof a crystalline form according to claim 1; wherein the neurological disease associated with acetylcholinesterase is selected from the group consisting of Alzheimer's disease, Parkinson's syndrome, epilepsy, and schizophrenia.

10. A pharmaceutical composition comprising: 2.0 mg of Form A according to claim 1, 22.0 mg of pre-gelatinized starch, 100.0 mg of microcrystalline cellulose, 5.0 mg of low substituted hydroxypropyl cellulose, and 1.0 mg of magnesium stearate.

* * * * *